United States Patent [19]
Skibo et al.

[11] Patent Number: 5,639,881
[45] Date of Patent: Jun. 17, 1997

[54] SYNTHESIS AND ELUCIDATION OF PYRIMIDO (4,5-Q) QUINAZOLINE DERIVATIVES

[75] Inventors: Edward B. Skibo, Scottsdale, Ariz.; Robert H. Lemus, Escondido, Calif.

[73] Assignee: Arizona Board of Regents acting on behalf of Arizona State University, Tempe, Ariz.

[21] Appl. No.: 763,375

[22] Filed: Nov. 8, 1991

[51] Int. Cl.$^6$ .................... C07D 487/04; C07D 239/90; A61K 31/505; C07B 43/02

[52] U.S. Cl. .................... 544/251; 544/287; 564/124; 564/153; 564/156; 560/22; 560/23

[58] Field of Search ................................ 544/251

[56] References Cited

PUBLICATIONS

Von Hoff, Journal of the NC1 82, p. 110 (Jan. 1990).
Von Hoff Journal of NIC 82, p. 96 (Jan. 1990).
Alberts, Proc. of AACR 28, Mar. 1987 p. 420.
Lemus, J. Org. Chem 57, 5649 (1992).

*Primary Examiner*—Mark L. Berch
*Attorney, Agent, or Firm*—Richard R. Mybeck

[57] ABSTRACT

Pyrimido[4,5-g]quinazoline quinone derivatives were synthesized as anthraquinone-like reductive alkylating agents. Like many naturally-occurring antibiotics, these quinone derivatives are designed to afford an alkylating quinone methide species upon reduction and leaving group elimination. Kinetic studies of pyrimido[4,5-g]quinazoline hydroquinones provided evidence of quinone methide intermediates able to trap nucleophiles (alkylation) and protons. The rate of quinone methide formation is determined by the hydroquinone free energy. Thus, a linear free energy relationship for quinone methide formation was obtained by plotting rates of quinone methide formation, as the log, versus the quinone reduction potential. The pyrimido[4-5-g]quinazoline quinone methides fall on this free energy plot, showing that these species are formed by the same mechanism as the other structurally-diverse quinone methides previously studied in this research group. A drawback of many quinone antibiotics, particularly the anthracyclines, is the formation of toxic oxygen species by quinone/hydroquinone cycling. In the present invention pyrimido[4,5-g]quinazoline hydroquinones are found to be relatively stable toward oxygen, and thus cause little oxygen toxicity. Antitumor screening revealed that the disclosed pyrimido [4,5-g]quinazoline dione derivatives possess excellent inhibitory activity against selected human cancer cell lines. The pyrimido[4,5g]quinazoline-diones have the following structural formulae:

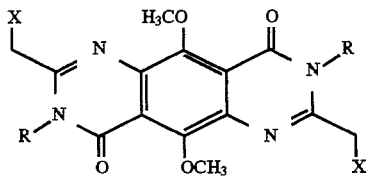

wherein:

R is H or $CH_3$; and X is Cl or Br.

11 Claims, 3 Drawing Sheets

SYNTHESIS AND ELUCIDATION OF PYRIMIDO (4,5-Q) QUINAZOLINE DERIVATIVES

This invention was made in part with government support under NCI/NIH Grant No. 2 RO1 CA 36876. The United States Government may have certain rights under the invention.

INTRODUCTION

The present invention relates to newly discovered compounds derived from the pyrimido[4,5-g]quinazoline ring system, methods of preparing the new compounds, and pharmaceutical preparations containing the compounds which are useful as antitumor agents especially in the treatment of breast cancer.

BACKGROUND OF THE INVENTION

The anthraquinone ring is present in many classes of antitumor agents including the anthracyclines, mitoxanthrone, and the recently discovered dynemicin A. In the case of mitoxantrone, intercalation of the anthraquinone ring into DNA and the external binding of the side chains are believed responsible for the antitumor activity of this drug. Additionally, intercalation of the anthraquinone portion of dynemicin A would serve to place the reactive enediyne moiety in position for strand cleavage. The utility of the anthraquinone ring as a vehicle for pharmacophores in these and other drugs prompted an investigation of the pyrimido [4,5-g]quinazolines as anthraquinone mimics. Presented herein are the synthesis, physical chemistry, and antitumor properties of these mimics.

The pyrimido[4,5-g]quinazoline-tetrone (quinone) systems were designed as reductive alkylating agents. Reductive alkylation involves the formation of an alkyating quinone methide species upon reduction of the quinone and elimination of a leaving group. Thus, reduction of the quinone would be followed by elimination of leaving group (s) to afford quinone methide species. Kinetic studies show that the quinone methide species formed in solution are capable of activity as nuceophile and electrophile traps. This finding is consistent with our previous studies of quinazoline-based quinone methides (See: Lemus, R. L. et al., *J. Org. Chem.* 1988, 53, 6099).

The interest in reductive alkylating agents stems from the possibility of selective activation of such agents in low reduction potential tumor cells (See: Keyes et al., *Adv. Enz. Reg.*, 1985, 23, 291). However, the major drawback of these agents is the production of cardiotoxic oxygen radicals (See: Doroshow, J. H., *Cancer Res.* 1983, 43, 460; and Begleiter, A., *Cancer Res.*, 1983, 43, 481), which result from cycling between the quinone and hydroquinone form of the agent. The pyrimido[4,5-g]quinazoline-tetrone mimics of the present invention are designed to remedy this problem. Reduction affords a hydroquinone stablized by internal hydrogen bonds (See: Skibo, E. B. et al., *J. Org. Chem.* 1988, 53, 420). The present invention provides kinetic evidence that such a hydroquinone is relatively stable to oxygen because of these hydrogen bonds.

The pyrimido[4,5-g]quinazoline diones were designed as non-redox-active antitumor agents. These analogues are much less reactive than the tetrone reductive alkylating agents and can only trap nucleophiles. For these reasons, the pyrimido[4,5-g]quinazoline diones exhibit cytotoxicity against human cancer cell lines while the tetrones (quinones) are inactive.

The present study of pyrimido[4,5-g]quinazoline based anthraquinone mimics demonstrates the value of preliminary physical studies (kinetics and electrochemistry) in the design of cytotoxic alkylating agents.

BRIEF SUMMARY OF THE DISCLOSURE

The present invention relates to the discovery and synthesis of pyrimido[4,5-g]quinazoline-tetrones and pyrimido [4,5-g]quinazoline-diones having the structure shown below. Both systems possess leaving groups so as to alkylate biologically important nucleophiles. The pyrimido[4,5-g] quinazoline tetrones are quinone derivatives functionalized with leaving groups to permit alkylation only in a low reduction potential environment (reductive alkylation). The corresponding dione derivatives do not possess the quinone functionality and, thus, are capable of alkylating in both high and low reduction potential environments.

The pyrimido[4,5-g]quinazoline-tetrones have the following structural formula:

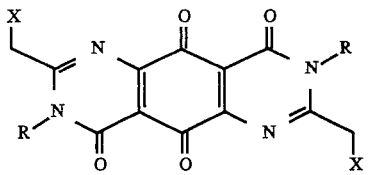

Wherein
R is H or CH₃
X is Cl or Br

The pyrimido[4,5-g]quinazoline-diones have the following sturctural formulae:

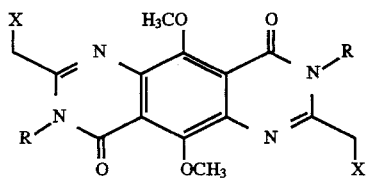

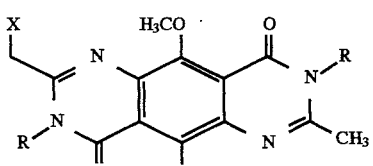

Wherein
R is H or CH₃
X is Cl or Br

DESCRIPTION OF PREFERRED EMBODIMENTS

Figure 1:
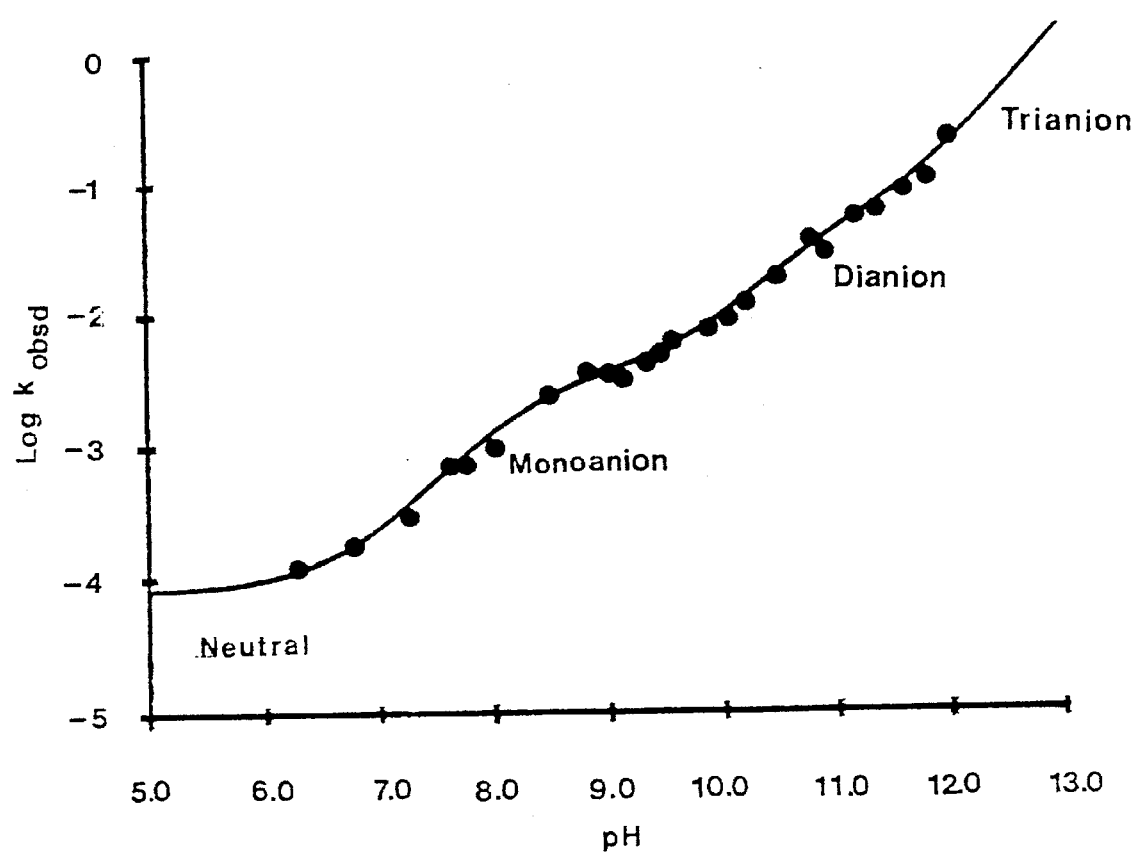
FIG. 1. Shows the pH-rate profile for the conversion of neutral 28 and its anionic forms to quinone methide and carbonation species in anaerobic aqueous buffer FIG. 2. Shows a linear free energy relationship for the quinone methide forming reactions in Table I. The x-axis is the log of the rate of quinone methide formation and the y-axis is the quinone reduction potential measured against the normal hydrogen electrode.

The present invention relates to the synthesis and elucidation of the pyrimido[4,5-g]quinazolines shown above and the details thereof shall now be described.

Pyrimido[4,5-g]quinazoline Synthesis. There are few reports of pyrimido[4,5-g]quinazolines in the literature. Although simple analogues were prepared after the turn of the century, this laboratory reported the first quinone derivatives in 1988 (Skibo et al., op.cit.). The strategy employed for the synthesis of pyrimido[4,5-g]quinazoline 4,5,9,10-tetrones(quinones) without leaving group centers (e.g., methoxymethyls or halomethyls) was to annelate both pyrimidinone rings to a nitrobenzene derivative. The nitro group was then reduced to the amine, from which the benzoquinone ring was synthesized by dichromate oxidation. In the presence of a leaving group center, dichromate oxidation results in oxidation of this center (e.g., methoxymethyl to carboxylic acid). Thus the pyrimido[4,5-g]quinazoline based reductive alkylating agents were prepared by annelating the pyrimidinone rings to a p-dimethoxybenzene derivative. The p-dimethoxy derivative was then readily converted to the desired quinone or hydroquinone derivative. The preparation of pyrimido[4,5-g]quinazoline reductive alkylating agents is described in Schemes I through V shown below.

Scheme I shows the preparation of the hexasubstituted benzene derivatives 6 and 7, which were starting materials for all pyrimido[4,5-g]quinazolines described herein. The nitration of 1 only afforded the mononitrated product 2, but the second nitration was possible after conversion of the nitrile groups to esters. Although nitration para to a nitro group would appear difficult, the conversion of 4 to 5 occurs under mild conditions. Perhaps the steric bulk of the esters forces the nitro group of 4 out of plane with the benzene ring thereby removing its resonance electron withdrawing capability.

Annelation of the pyrimidinone ring to 6 or 7, as shown in Scheme II, afforded the pyrimido[4,5-g]quinazolinedione derivatives 14–17. The pyrimido [4,5-g]quinazolinediones, 16 and 17 are excellent antitumor agents.

The pyrimido [4,5-g]quinazoline-tetrones, were prepared as illustrated in Scheme III. In the case of the N-unsubstituted derivative 14, O-demethylation and dephenoxylation to afford 18 were readily carried out by $BBr_3$ treatment. The steric bulk of the N-methyl substituents required the use of the methoxymethyl derivative 15 rather than the phenoxymethyl derivative, however. In the phenoxymethyl analogue of 15, no dephenoxylation occurs on treatment with $BBr_3$ since bromide cannot attack the sterically hindered methylene centers. In 15, bromide attack occurs only at the methyl centers to afford 20 as the product. Methanesulfonyl chloride treatment of 20 provided the desired chloromethyl derivative 21.

Schemes IV and V describe the preparation of N-unsubstituted and N-methylated hydroquinone analogues bearing only one leaving group, 28 and 35, respectively. The hydrolysis of these hydroquinones was studied in order to gain mechanistic insights into quinone methide formation and fate. The synthetic steps in Schemes IV and V are straightforward, but the conditions for the final steps (27→28 and 34→35) are noteworthy. Hydroquinone 28 is stabilized by internal hydrogen bonds, and thus the demethylation/dephenoxylation and halide exchange steps smoothly convert 27 to 28. Hydroquinone 35, on the other hand, is not stabilized by internal hydrogen bonds. This hydroquinone rapidly eliminates HCl in any protic solvent to afford the quinone methide, which ketonizes to the tetramethyl derivative (vide infra). The stable quinone 34 was converted to 35 in chloroform solvent by shaking with aqueous dithionite for 30 seconds. The hydrolytically labile 35 was isolated from the chloroform layer in sufficiently pure form for our kinetic studies.

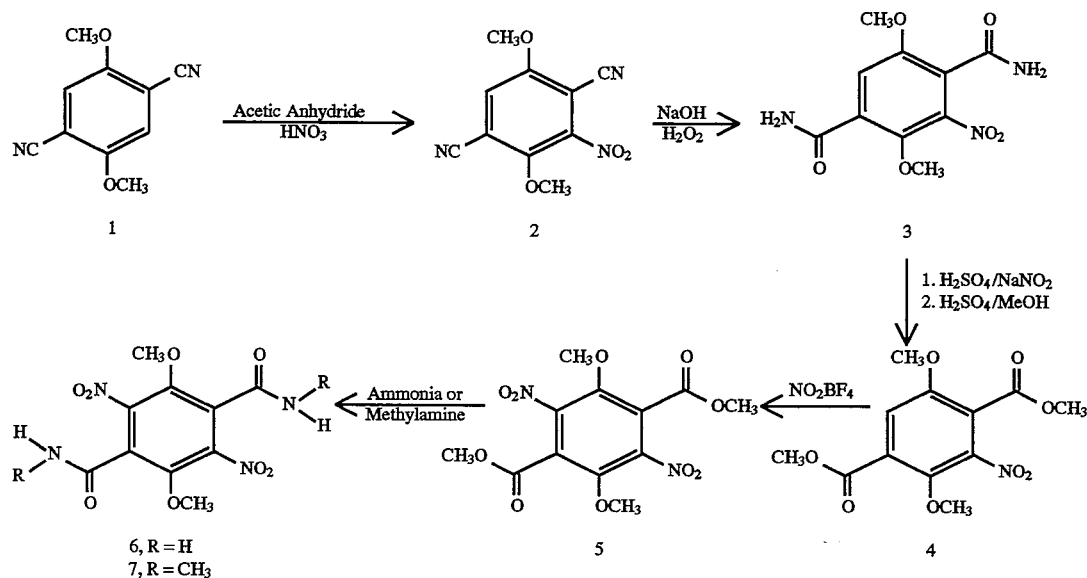

SCHEME I

SCHEME II
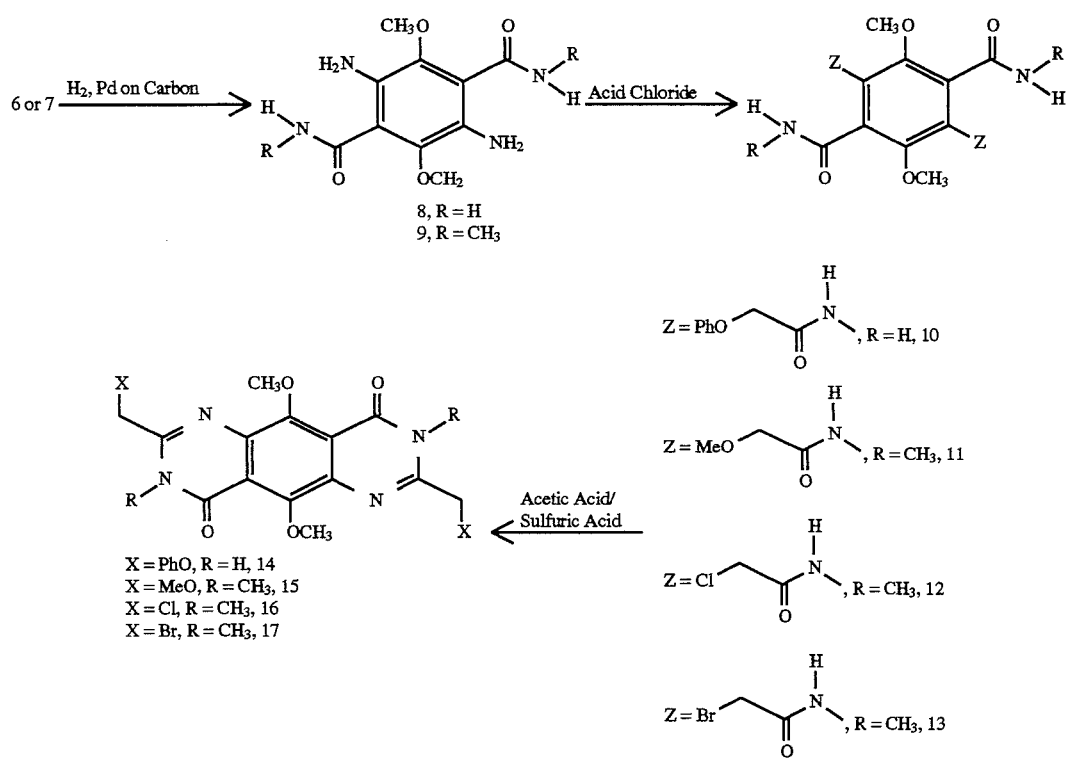
SCHEME III
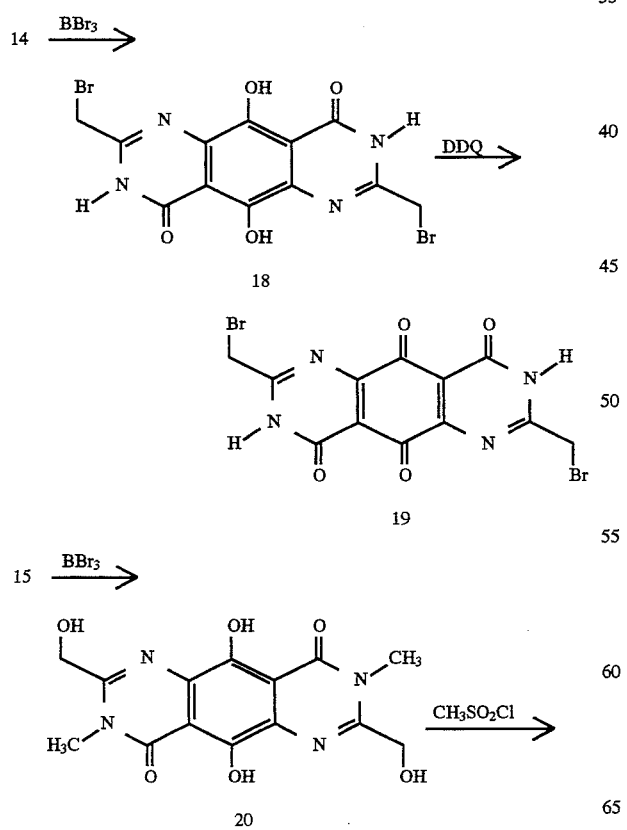
-continued
SCHEME III
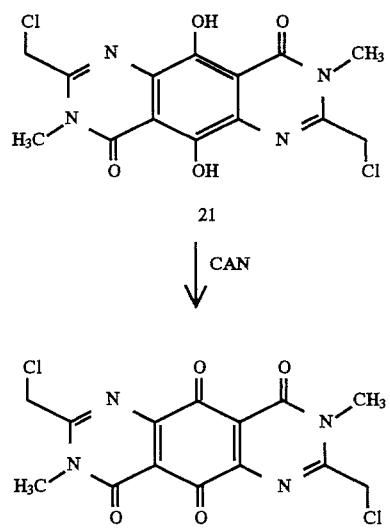

5,639,881
SCHEME IV
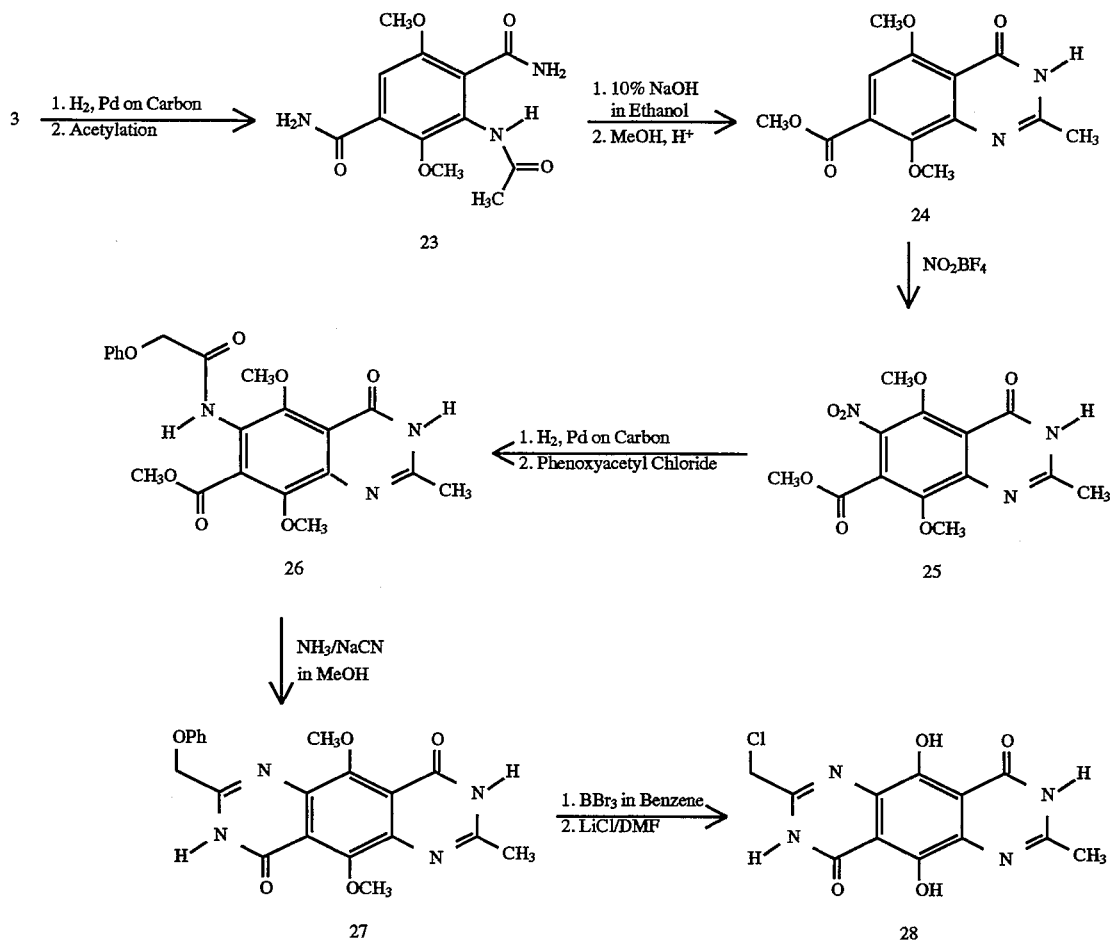
SCHEME V
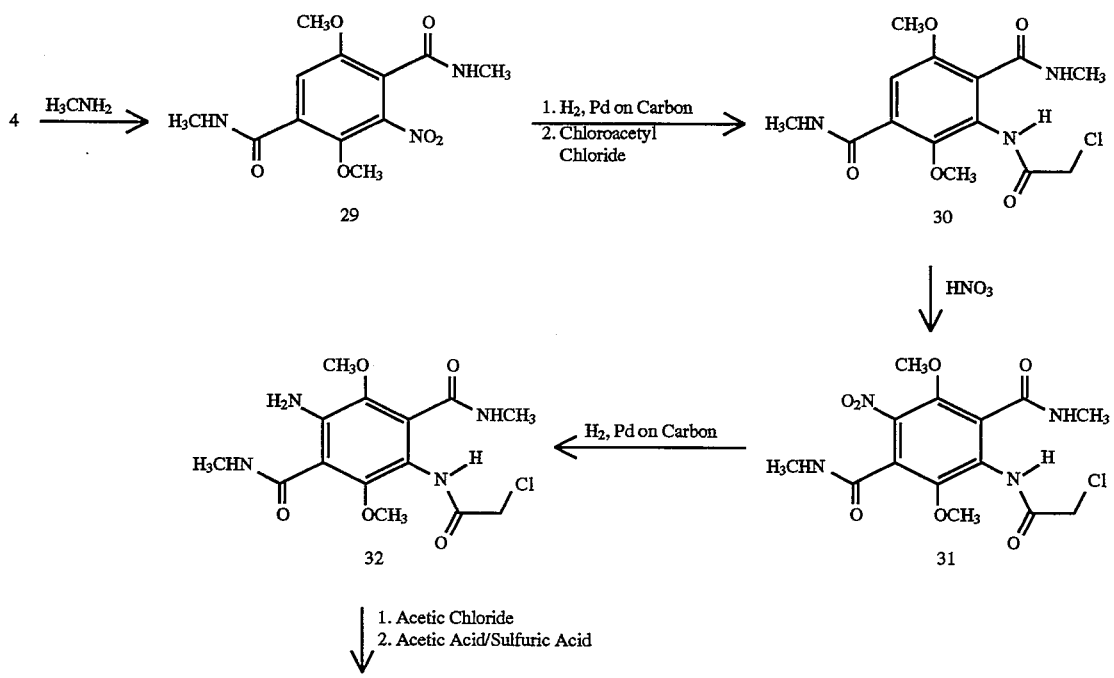

-continued
SCHEME V

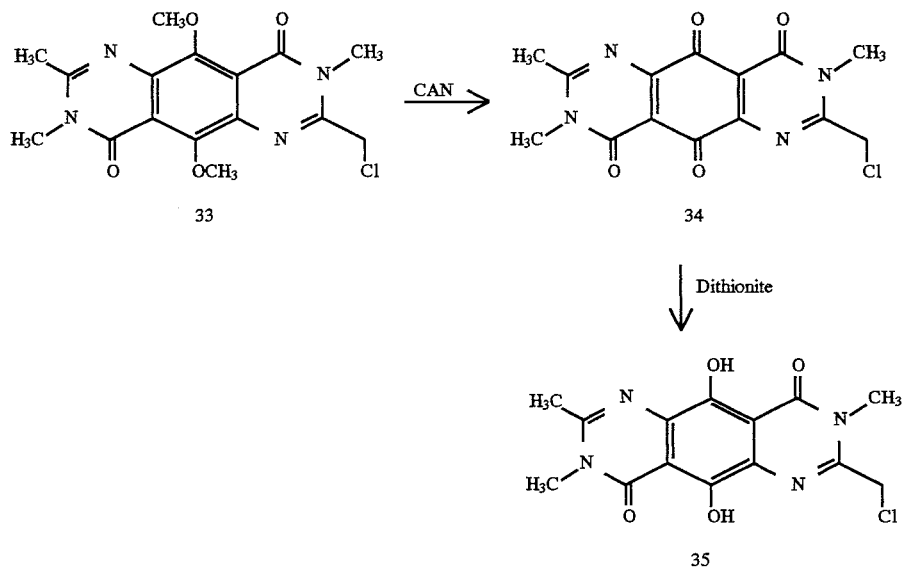

Quinone Methide Chemistry. Insights into the formation and fate of pyrimidoquinazoline quinone methides were obtained from hydrolytic studies of hydroquinones 28 and 35. Both hydroquinones eliminate the chloride leaving group to afford a reactive quinone methide species capable of trapping nucleophiles and electrophiles. Details of quinone methide formation and fate were obtained from pH-rate profiles, from trapping studies with added 2-mercaptoethanol, and from product studies.

The hydrolysis of 28 was followed spectrophotometrically at 430 nm in anaerobic aqueous buffer over a pH range of 6 to 12 with $[28]=5\times10^{-5}$M. Absorbance vs. time plots for hydrolysis are first order in character, with the first-order rate constants ($k_{obsd}$) independent of buffer concentration but dependent on pH as shown in FIG. 1. The use of known hydroquinone and quinone extinction coefficients at 430 nm permitted the calculation of product yields: 69±1% 38 and 31±1% 39 regardless of the pH (product structures shown in Scheme VI). The accuracy of the yield determinations was enhanced by the intense hydroquinone visible spectrum and the absence of visible absorbances for the quinone derivative. Product isolation studies confirmed the presence of 39.

The mechanism of 38 and 39 formation from 28 is discussed in conjunction with Scheme VI. The pH-rate data in FIG. 1 indicate that rate-determining chloride elimination occurs from the neutral, monoanion, dianion, and trianion forms of 28. Plateaus corresponding to the first three eliminations are indicated on FIG. 1. The increasing rates above pH 11 may pertain to equilibrium trianion formation and rate-determining elimination of chloride from the trianion. Consideration of rate-determining chloride elimination from the various forms of 28 provides the rate law shown in equation 1

$$k_{obsd} = k_1 + \frac{k_2 K_{a1}}{K_{a1}+a_H} + \frac{k_3 K_{a2}}{K_{a2}+a_H} + \frac{k_4 K_{a3}}{a_H} \quad \text{Equation 1}$$

where the rate and equilibrium constants are those shown in Scheme VI. The numerical values for these constants (shown in Scheme VI) were obtained by computer-fitting the data in FIG. 1 to equation 1. The solid line in FIG. 1 was then generated from equation 1 substituted with these constants. The independently determined $pK_a$ for monoanion formation (8.26±0.15) is in agreement with the kinetic $pK_a$ value (8.3). Thus, the kinetically-determined $pK_a$ values in Scheme VI represent actual acid dissociations rather than mixtures of constants.

SCHEME VI

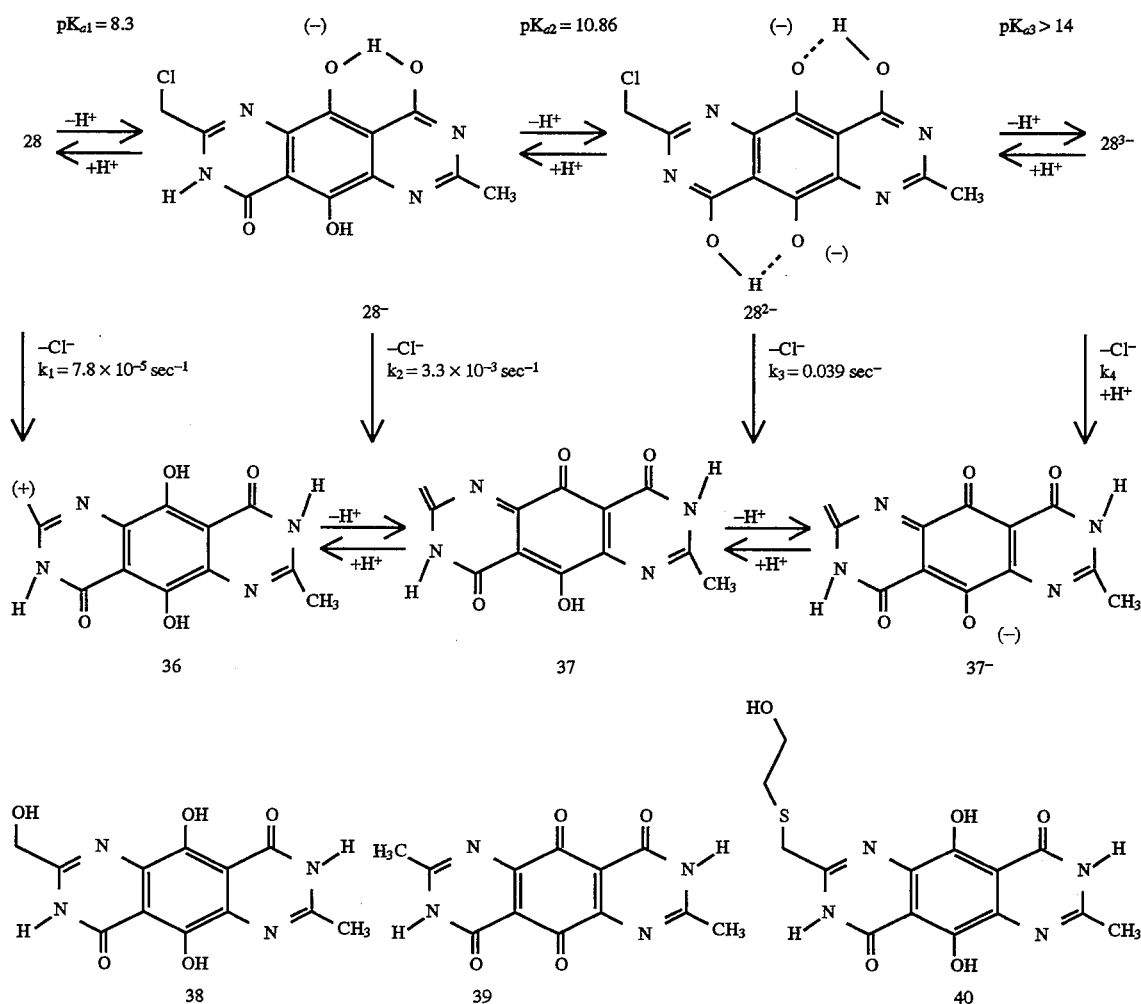

Chloride elimination from the neutral and anionic forms of 28 affords an equilibrating mixture of protonated (36), neutral (37), and anionic (37⁻) quinone methides. Proton trapping by 37⁻, in competition with water trapping of 36 and 37, then affords a mixture of 38 and 39. Evidence of steady-state intermediates capable of trapping nucleophiles (36 and 37) was obtained by adding 10 to 100X excess of 2-mercaptoethanol over 28. The observed rate constants are independent of [2-mercaptoethanol] and are essentially the same as that measured for hydrolysis of 28 in the absence of this nuceophile. The presence mercaptoethanol results in formation of a hydroquinone (nucleophile-trapped) product 40 and no quinone 39, however. Thus, quinone methide formation must occur in a rate determining step, followed by its relatively rapid trapping by the mercaptide nuceophile. The mercaptoethanol trapping studies of benzimidazole (See: Skibo, E. B., *J. Org. Chem.* 1986, 51, 522) and quinazoline (See: Lemus et al., op. cit.) based quinone methides likewise provided evidence of a steady-state species.

The hydrolysis of 35 in anaerobic buffer proceeds by a first-order process to afford 42 as the sole product. In contrast to 28, the hydrolysis of 35 occurs at stopped-flow rates much above pH 8. The pH-rate profile, obtained over the pH range of 5 to 8, is a straight line of slope +1. This profile is attributed to equilibrium hydroxyl anion formation $(35 \rightleftharpoons 35^- + H^+, pK_a = 10.3)$ and loss of chloride under the condition of pH<10.3, Scheme VII. Computer fitting the pH-rate data to $k_{obsd} = k_1 K_{a1}/a_H$, and substituting $pK_{a1} = 10.3$, provides and elimination rate constant of $k_1 = 24$ sec$^{-1}$.

The influence of internal hydrogen bonds on quinone methide formation is apparent from the hydrolysis studies discussed above. Internal hydrogen bonding lowers the free energy of 28 and its anionic forms resulting in slow chloride eliminations, Scheme VI. In contrast, 35 cannot form internal hydrogen bonds and the elimination of chloride occurs with facility (compare $k_1 = 3.3 \; 10^{-3}$ sec$^{-1}$ for elimination of chloride from 28⁻ with 24 sec$^{-1}$ for the same elimination from 35⁻). Internal hydrogen bonding also influences the quinone methide trapping products: the quinone methide species from 28 traps nucleophiles and protons (ratio of 69:31) while the quinone methide from 35 traps only protons. Previous work in this laboratory showed that quinone methide trapping is under thermodynamic control. Stabilization of the hydroquinone by internal hydrogen bonding favors nuceophile trapping since a hydroquinone (38) is the product. Without internal hydrogen bonds electrophile trapping is favored since a stable quinone (39) is the product.

SCHEME VII

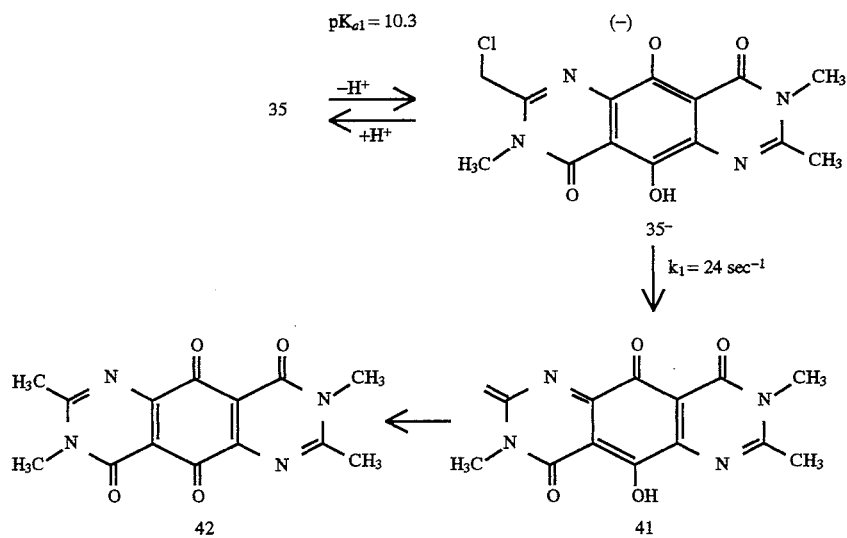

Linear Free Energy Relationship For Quinone Methide Formation. This relationship was obtained by plotting the log of first-order rate constants for quinone methide formation vs two-electron quinone reduction potentials, FIG. 2. The quinone reduction potential is a measure of the free energy difference between the quinone and hydroquinone forms of the redox couple, and thus it can be used as an indirect measure of hydroquinone free energy. Data points for the linear free energy plot were obtained as discussed below in conjunction with Scheme VIII.

Shown in the inset of Scheme VIII is an elimination reaction from $28^-$ to afford a quinone methide species. The first-order rate constant for this reaction was obtained from the pH-rate data in FIG. 1. The corresponding reduction potential, $39^-/43^-$, was obtained from a previously published Nernst Clark plot. All the quinone reduction potentials in the linear free energy plot were obtained with quinone systems without the leaving group present. The reduction potential is read off a Nernst Clark plot at a pH value where the particular hydroquinone species (neutral, monoanion, or dianion) is reversibly formed.

Figure 2:
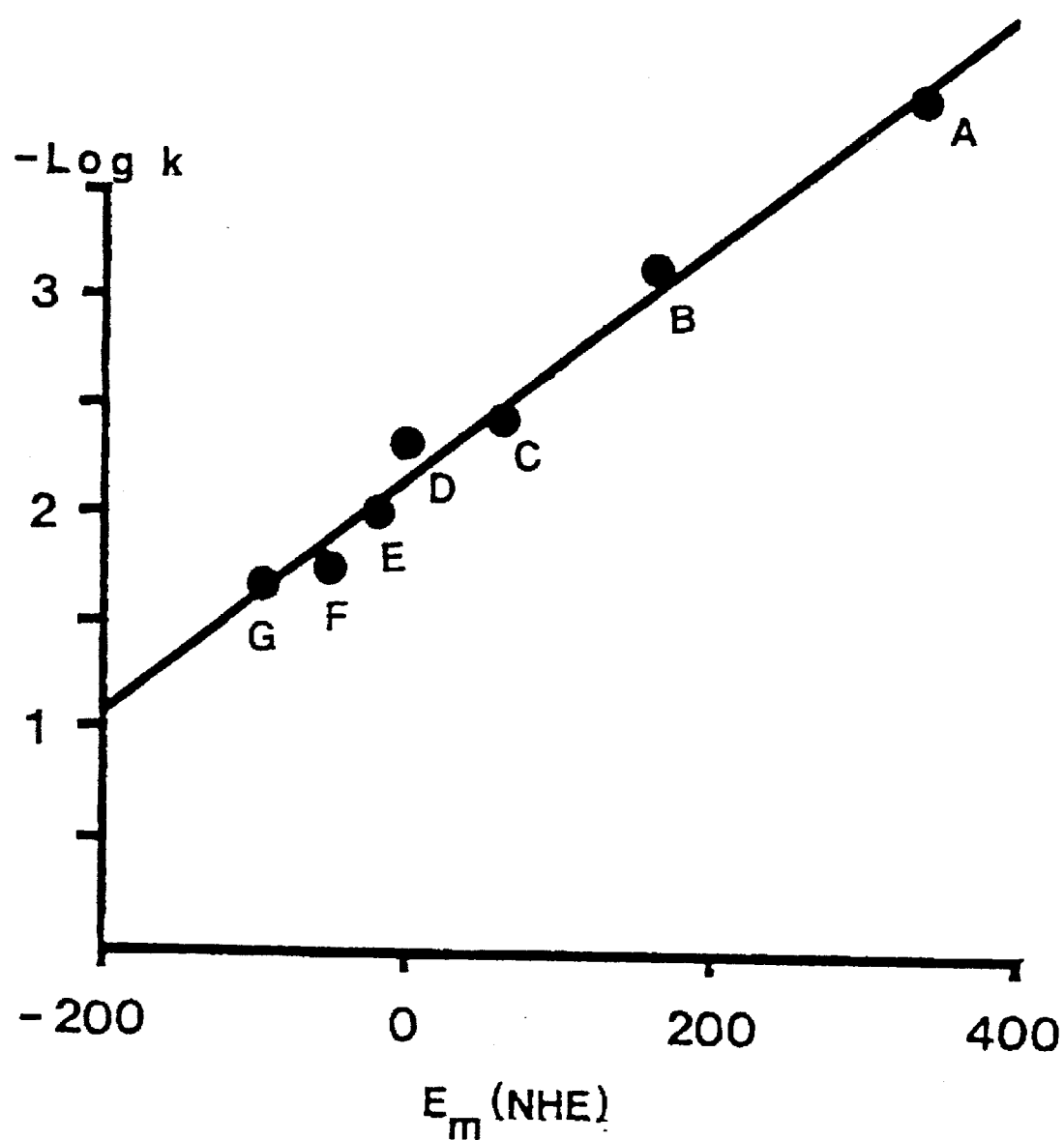

The reactions used to obtain the plot in FIG. 2 are found in Table I. There is an excellent correlation of Log k with the quinone reduction potential, even though the reactivity range spans 0.5 volts and a structural diversity of quinone methides are included. It is apparent from the excellent correlation that all the reactions involve an elimination of the leaving group in the rate determining step. A substitution reaction, such as the conversion of 28 to 40, must necessarily involve elimination of the leaving group followed by nucleophile trapping of the intermediate, and not an $S_N2$-type process.

SCHEME VIII

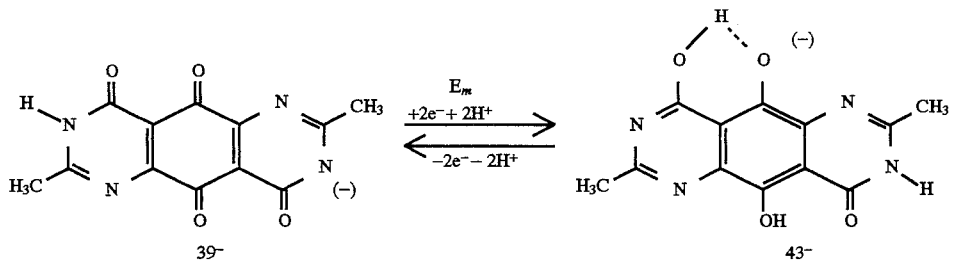

-continued
SCHEME VIII
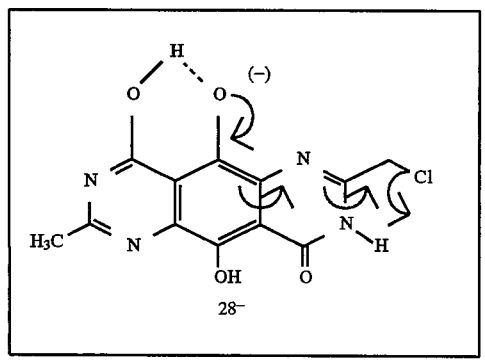
TABLE I
| ENTRY | REACTION | REFERENCE |
|---|---|---|
| A | 28 → 36 | This Study |
| B | (structure) → (structure) | 8a |
| C | 28⁻ → 37 | This Study |
| D | (structure) → (structure) | 15 |
| E | (structure) → (structure) | 8a |
| F | (structure) → (structure) | 8b |
| G | 28²⁻ → 37⁻ | This Study |

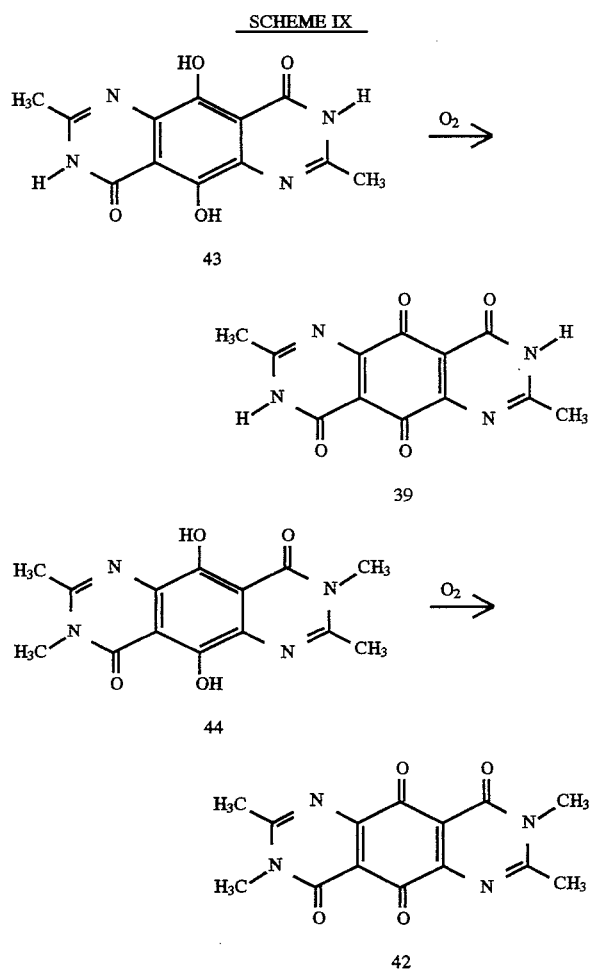

SCHEME IX

Figure 3:
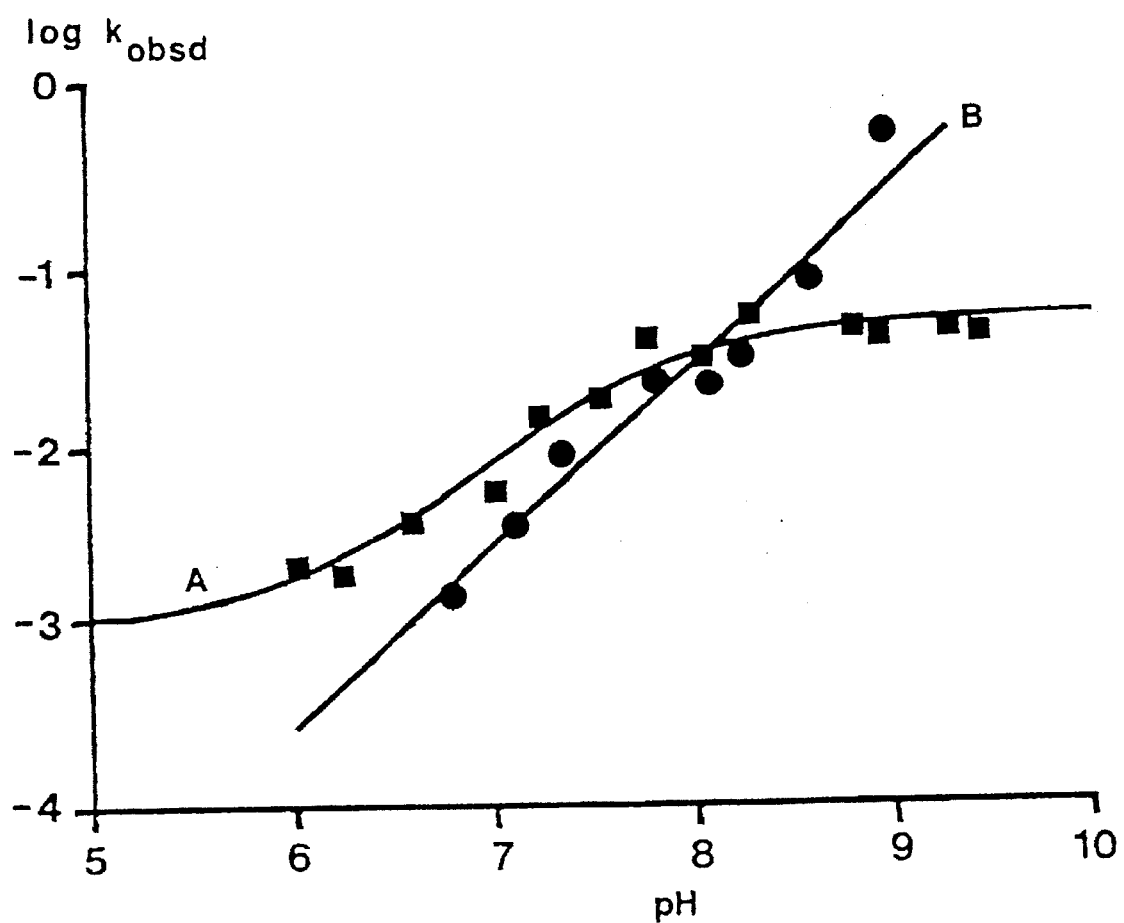
FIG. 3. Shows the pH-rate profiles or air oxidation of hydroquinones 43 (Plot A) and 44 (Plot B) in aerobic aqueous buffer.

Oxygen Reactivity. In order to assess the capability of the title systems to generate reactive oxygen species by quinone/hydroquinone cycling, the rate laws were determined for oxygen oxidation of 43 and 44, Scheme IX. These respective hydroquinones are analogues of 28 and 35 without leaving groups present. As expected, the internal hydrogen bonds of 43 slow oxidation at high pH while the absence of hydrogen bonds in 44 result in stopped flow oxidations under these conditions. However, the crossing of the pH-rate profiles near neutrality (FIG. 3) results in similar rates of oxidation for both systems at physiological pH.

In aerobic aqueous buffer, both 43 and 44 are converted to the corresponding quinones {Scheme IX) by first-order processes. Inspection of the pH-rate profile for the oxidation of 43, Plot A in FIG. 3, reveals that the neutral and monoanion form as of this hydroquinone are oxidized to quinone 39. The solid curve of Plot A was generated from the rate law, $k_{obsd}=k_1+k_2K_{a1}/(a_H+K_{a1})$, where $k_1$ is the rate of oxidation of the neutral species ($1\times10^{-3}$ sec$^{-1}$), $k_2$ is the rate of oxidation of the hydroquinone monoanion (0.046 sec$^{-1}$), $pK_{a1}$ is the acid dissociation constant (7.78), and $a_H$ is the proton activity determined with a pH meter. The acid dissociation constant obtained from the pH-rate data is nearly the same as the value determined previously, 8.26±0.15.1

In contrast to 43, the oxidation of 44 to 42 occurs at stopped flow rates at or above pH 9. The pH-rate profile possesses a slope of one, Plot B of FIG. 3, which may reflect equilibrium hydroquinone monoanion formation followed by oxidation. If this is the case, the monoanion of 44 oxidizes to 42 at 5.8 sec$^{-1}$ (based on the pKa of 10.3 for 44).

From the foregoing, it is apparent that internal hydrogen bonding interactions can substantially slow the oxidation of a hydroquinone monoanion. Thus 43$^-$ oxidizes 128-fold slower than 44$^-$. The crossing of the pH-rate profiles in FIG. III results in similar rates of oxidation for both systems at physiological pH: 43 oxidizes at $1.7\times10^{-2}$ sec$^{-1}$ while 44 oxidizes at $9\times10^{-3}$ sec$^{-1}$. Both hydroquinone systems are still more stable toward oxygen than reduced anthracyclines, which rapidly oxidize on mixing with air. These observations suggest that pyrimido[4,5-g]quinazoline reductive alkylating agents will show little cardiotoxicity. In fact, it has been shown that reducing the capability of an anthracycline to cycle between reduced and oxidized forms (as is the case with 5-iminodaunorubicin), does reduce cardiotoxicity.

Antitumor Studies. From the studies described above, it was predicted that the pyrimido [4,5,g]quinazoline reductive alkylating agent 19 would possess antitumor activity. This system affords an alkylating quinone methide species upon reduction and its tricyclic structure resembles anthracylines and other antitumor agents. Screening studies against colon and breast cancers revealed that 19 actually possesses poor activity, $IC_{50}>10^{-6}M$ ($IC_{50}$ is the concentration needed to inhibit 50% of treated cells). A probable reason for the inactivity of 19 is its conversion to an anion near neutrality (pKa=6.5) thereby precluding its entry into a cell. Although the N-methylated analogue 22 cannot form an anion, it too is inactive, perhaps because the quinone methide formed upon reduction is only capable of trapping protons (see Scheme VII).

If anion formation and chemical reactivity are important factors in pyrimido[4,5-g]quinazoline antitumor activity, then the analogues 16 and 17 should be antitumor agents. Both analogues are lipophilic and both will not ionize at physiological pH. Furthermore, both analogues will alkylate nucleophiles by an $S_N1$ mechanism without competing proton trapping. The presumed $S_N1$ mechanism is based on reactivity of 28, which spontaneously eliminates chloride to afford a carbocation (Scheme VI). Assays of 16 and 17 against colon and breast cancers in fact revealed excellent antitumor activity, $IC_{50}$ values as low as 20 nM. Preliminary studies suggest that 16 and 17 act as monoalkylating agents (at least one alkylating center is necessary for activity), and that the methoxy groups are also necessary for activity. The latter observation is consistent with an $S_N1$ alkylation mechanism, which requires resonance electron donation by the methoxy groups to stabilize the carbocation.

Experimental Section

All analytically pure compounds were dried under high vacuum at room temperature or in a drying pistol heated with refluxing methanol. Compounds susceptible to decomposition (hydroquinones) were not heated above room temperature. Some of the compounds still contained water of crystallization that was determined from the elemental analyses found.

Uncorrected melting and decomposition points were determined with a MEL-TEMP apparatus. All TLC was run with MERCK silica gel 60 ($F_{254}$) plates, employing a variety of solvents. IR spectra were taken as KBr pellets or thin films; the strongest IR absorbances are reported. $^1$H NMR spectra were obtained on a BRUKER AM-400 spectrometer, and chemical shifts are reported relative to TMS.

Kinetic Studies of Hydrolysis and Oxidation. The hydrolytic studies of 28 and 35 were carried out in anaerobic aqueous buffer, and the reoxidation studies of 43 and 44 were carried out in aerobic aqueous buffer at 30.0°±0.2° C.

The anaerobic experiments were carried out with Thunberg cuvettes as previously described. A dimethyl sulfoxide stock of the compound to be studied was prepared fresh, and 50 µL of this stock was added to 2.95 mL of buffer. The absorbance vs time data were obtained on a PERKIN-ELMER 559 or a Lambda-3 UV-vis spectrophotometer and fit to a first-order rate law.

Synthesis and physical properties of new compounds are provided below:

3,6-Dicyano-1,4-dimethoxy-2-nitrobenzene(2. A suspension consisting of 30 mL of acetic anhydride and 995 mg (5.29 mmol) of 1 was chilled to 0° C. To the chilled suspension, 15 mL of 90% nitric acid was added portionwise so as to maintain a reaction temperature less than 20° C. After the addition was completed, the reaction was left to stir at room temperature for 15 minutes and then poured over ca 500 g of crushed ice. The resulting yellow precipitate was filtered off and washed with cold water. The solid was recrystallized by dissolution in a minimum amount of chloroform followed by addition of hexane: 870 mg (71%) yield; mp 146°–147° C.; TLC (ethyl acetate), $R_f$=0.611 IR (KBr pellet) 2239, 1552, 1490, 1403, 1365, 1276, 1249, 1041, 962, 925 cm$^{-1}$; $^1$H NMR (dimethyl-d$_6$ sulfoxide) δ8.24 (1H, s, 5-H), 4.04 (6H, s, methoxys); mass spectrum (EI), m/z 233 (P+). Anal. Calcd for $C_{10}H_7N_3O_4$ 0.25 $H_2O$: C, 50.53; H, 3.18; N, 17.67. Found: C, 50.98; H, 2.95; N, 17.61.

3,6-Dicarbamyl-1,4-dimethoxy-2-nitrobenzene(3). To 508 mg (2.18 mmol) of 2 in 10 mL of ethanol, preheated to 40° C., were added 5 mL of 1 N NaOH and then 5 mL of 10% hydrogen peroxide. After a reaction time of ca 5 minutes, a yellow solid crystallized from solution. After heating for an additional 15 minutes, the solution was poured over 50 mL of ice water. The solid which resulted was filtered, washed with water, and then ethanol to afford the product as a pure white-colored solid: 470 mg (80%) yield; mp 288°–290° C.; TLC (chloroform/methanol [9:1]), $R_f$=0.23; IR (KBr pellet) 3374, 3186, 1657, 1627, 1535, 1482, 1473, 1423, 1237, 1031 cm$^{-1}$; $^1$H NMR (dimethyl-d$_6$ sulfoxide) δ7.97 and 7.84 (4H, 2 brs, 3- and 6-carbamyls, no assignments made), 7.39 (1H, s, 5-H), 3.87 and 3.78 (6H, 2 s, 1- and 4-methoxys, no assignments made); mass spectrum (EI mode) m/z 269 (P+). Anal. Calcd for $C_{10}H_{11}N_3O_6$: C, 44.62, H, 4.12; N, 15.61. Found: C, 44.45; H, 4.02; N, 15.47.

1,4-Dimethoxy-2-nitrobenzene-3,6-dicarboxylic Acid Dimethyl Ester (4) was prepared by the following two-step procedure:

To 100 mL of concentrated sulfuric acid, was added 3.0 g (11 mmol) of 3 at room temperature. The reaction mixture was stirred at this temperature until the solid was fully dissolved, and then the mixture was chilled to 0° C. To the chilled reaction mixture, a solution consisting of 6 g sodium nitrite in 60 mL water was added portionwise below the surface of the solution while maintaining a reaction temperature below 25° C. After complete addition, the reaction mixture was heated at 70° C. until effervescence had ceased and then poured over ca 500 g of crushed ice. The solid was filtered and washed with water to afford the off-white dicarboxylic acid derivative: 2.2 g (73%) yield; TLC (isopropanol/water/ammonia [7:1:2]), $R_f$=0.49; $^1$H NMR (dimethyl-d$_6$ sulfoxide) δ7.64 (1H, s, 5-H), 3.90 and 3.82 (6H, 2 s, 1- and 4-methoxys, no assignments made); mass spectrum (EI mode), m/z 271 (P+).

To a solution of 4.0 g (0.015 mmol) of the product obtained above in 100 mL of dry methanol, was added 5 mL of concentrated sulfuric acid and the resulting mixture refluxed until TLC showed the reaction to be complete. The solvent was evaporated in vacuo to afford ca 25 mL of a yellow liquid. After pouring the liquid into 200 mL of ice-water, the resulting mixture was extracted with 3×100 mL portions of chloroform. The extracts were rinsed with 10% sodium carbonate and then with water. Drying ($Na_2SO_4$) the extracts and removal of the solvent in vacuo afforded a residue which crystallized as yellow flakes upon addition of hexane: 3.3 g (75%)yield; mp 91°–92° C.; TLC (isopropanol /water/ammonia [7:1:2]), $R_f$=0.83; IR (KBr pellet) 2957, 1734, 1536, 1487, 1450, 1254, 1233, 1141, 1096 cm$^{-1}$; $^1$H NMR (dimethyl-d$_6$ sulfoxide) δ7.73 (1H, s, 5-H), 3.93, 3.92, 3.83 and 3.82 (12H, 4 s, methoxys, no assignments made); mass spectrum (EI mode), m/z 299 (P$^+$). Anal. Calcd for $C_{12}H_{13}NO_8$: C, 48.17; H, 4.38; N, 4.68. Found; C, 47.82; H, 4.33; N, 4.77.

1,4-Dimethoxy-2,5-dinitrobenzene-3,6-dicarboxylic Acid Dimethyl Ester (5): To 5.0 g (0.017 mol) of 4 dissolved in 100 mL of dry acetonitrile, $NO_2BF_4$ was added until no starting material was evident by TLC. The solvent was removed in vacuo and the oily residue treated with 100 mL of ice water. The resulting mixture was extracted with 3×100 mL portions of ethyl acetate. The extracts were dried ($Na_2SO_4$) and evaporated in vacuo to a solid residue, which upon recrystallization from ethanol afforded 5 as yellowish-white needles; 3.8 g (66%) yield; mp 126°–127° C.; TLC (chloroform), $R_f$=0.52; IR (KBr pellet) 1746, 1548, 1480, 1439, 1388, 1361, 1291, 1197, 1150, 1027 cm$^{-1}$; $^1$H NMR (dimethyl-d$_6$ sulfoxide) δ3.93 and 3.90 (12H, 2 s, methoxys, no assignments made); mass spectrum (EI), m/z 344 (P$^+$). Anal. Calcd for $C_{12}H_{12}N_2O_{10}$: C, 41.87; H, 3.51; N, 8.14. Found C, 41.79; H, 3.25; N, 7.96.

3,6-Dicarbamyl-1,4-dimethoxy-2,5-dinitrobenzene (6): To a 100 mL of saturated methanolic ammonia was added 704 mg (2.05 mmol) of 5 and the reaction mixture left to stir at room temperature for 12 hours. After evaporating off the solvents, the solid residue was collected and washed with ethanol to give the desired compound as a white solid; 467 mg (73%) yield; dec pt 291°–293° C. TLC (isopropanal/ water/ammonia [7:1:2], $R_f$=0.78; IR (KBr pellet) 3444, 3424, 3313, 3191, 1674, 1660, 1542, 1402, 1020 cm$^{-1}$; $^1$H NMR (dimethyl-d$_6$ sulfoxide) δ8.42 and 8.23 (4H, 2 s, 3 and 6 carbamyls, no assignments made), 3.87 (6H, s, methoxys); mass spectrum (EI mode), m/z 314 (P$^+$); Anal. Calcd for $C_{10}N_{10}N_4O_8$: C, 38.25; H, 3.21; N, 17.83. Found; C, 38.65; H, 3.04; N, 17.53.

3,6-Bis(methylcarbamyl)-1,4-dimethoxy-2,5-dinitrobenzene (7). To a 67% w/w solution of methylamine in methanol, cooled to −78° C., was added 4.0 g (0.012 mol) of 5. After allowing the solution to come to room temperature over a period of 1 hour, the precipitated product was filtered off and rinsed with ethanol and then chloroform to afford the desired compound as a white solid: 2.9 g (73%) yield; dec pt 297°–299° C.; IR (KBr) 3293, 1655, 1570, 1536, 1474, 1416, 1396, 1373, 1059, 998 cm$^{-1}$; $^1$H NMR (dimethyl-d$_6$ sulfoxide) δ8.99–8.94 (2H, m, 3- and 6-carbamyl protons) 3.82 (6H, s, methoxys), 2.77 (6H, d, J=3.3 Hz, 3- and 6-carbamyl methyls); mass spectrum (EI mode), m/z 342 (P$^+$). Anal. Calcd for $C_{12}H_{14}N_4O_8$: C, 42.11; H, 4.12; N: 16.37. Found C, 42.32; H, 4.01; N, 15.76.

3,6-Dicarbamyl-1,4-dimethoxy-2,5-diaminobenzene (8): A mixture consisting of 561 mg (1.79 mmol) of 6, 50 mg of 5% Pd/C, and 100 mL of methanol was shaken under 50 psi of $H_2$ for 4 hours. Upon completing the reduction, 10 mL of concentrated hydrochloric acid was added immediately to the reaction mixture with stirring. After filtering the acidified mixture through CELITE and washing with methanol, the solvents were evaporated in vacuo and the solid residue thoroughly dried. The 8·2HCl was purified by dissolution in a minimum amount of hot methanol followed by addition of ethyl acetate: 568 mg (97%) yield; TLC (n-butanol/acetic acid/water [5:2:3]), $R_f$=0.37; $^1$H NMR (dimethyl-$d_6$ sulfoxide) δ7.93 and 7.92 (4H, 2 brs, 3- and 6-carbamyls, no assignments made), 3.69 (6H, s, methoxys); mass spectrum (EI mode), m/z 254 (P$^+$).

3,6-Bis(methylcarbamyl)-1,4-dimethoxy-2,5-diaminobenzene (9): A mixture consisting of 978 mg (2.84 mmol) of 7, 100 mg 5% Pd/C, and 100 mL of methanol was shaken under 50 psi of $H_2$ for 4 hours. Upon completing the reduction, 10 mL of concentrated hydrochloric acid was added to the reaction mixture with stirring. After filtering the solution through CELITE and washing the filtrate with methanol, the solvent was removed in vacuo and the residue dried for several hours. The dihydrochloride salt of 9 was recrystallized by dissolution in a minimum amount of hot methanol followed by cooling and then addition of ethyl acetate: 893 mg (88%) yield; TLC (n-butanol/acetic acid/water [5:2:3]), $R_f$=0.44; $^1$H NMR (dimethyl-$d_6$ sulfoxide) δ8.40 (2H, brs, 3- and 6-carbamyl proton), 3.64 (6H, s, methoxys), 2.81 (6H, d, J=4.0 Hz, 3- and 6-carbamyl methyls); mass spectrum (EI mode), m/z 282 (P$^+$).

2,5-Bis(phenoxyacetamido)-3,6-dicarbamyl-1,4-dimethoxybenzene (10): To the 568 mg ( 1.74 mmol ) 8.2HCl, suspended in 50 mL of dry benzene, were added 0.6 mL (4.34 mmol) phenoxyacetyl chloride and 2.4 mL (17 mmol) of dry triethylamine. The resulting mixture was stirred under a dry atmosphere at room temperature for 4 hours. The solvents were evaporated in vacuo using minimal heating and the residue treated with water to precipitate 10. The product was recrystallized from dimethyl formamide and then washed with water: 699 mg (77%) yield; mp 272°–274° C.; TLC (ethyl acetate/methanol [9:1]), $R_f$=0.32; IR (KBr pellet) 3385, 3262, 1701, 1680, 1600, 1551, 1492, 1456, 1367, 1222 cm$^{-1}$; $^1$H (dimethyl-$d_6$ sulfoxide) δ9.17 (2H, s, 2- and 5-acetamido NH), δ7.62, 7.57, 7.49 and 7.25 ( 4H, 4 brs, 3- and 6-carbamyls, no assignments made), 7.34 (4H, t, J=8.1 Hz, aromatic, no assignment), 7.0 (6H, d, J=8.5 Hz, aromatic, no assignments made); 4.61 (4H, s, methylenes), 3.68 and 3.58 (6H, 2 s, 1- and 4-methoxys, no assignments made); mass spectrum (EI mode) m/z 522 (P$^+$). Anal. Calcd for $C_{26}H_{26}N_4O_8$· 0.1 $H_2O$: C, 59.56, H, 5.04; N, 10.69. Found: C, 59.54; H, 5.12; N, 11.06.

2,5-Bis(methoxyacetamido)-3,6-bis(methylcarbamyl)-1,4-dimethoxybenzene (11): To 1.0 g (2.82 mmol) of 9.2HCl, dissolved in 50 mL of dry dimethyl formamide, were added 0.57 mL (6.24 mmol) of methoxyacetyl chloride and 1.1 mL (13.6 mmol) of dry pyridine. The resulting mixture was stirred at room temperature for 4 hours. After removing the dimethyl formamide in vacuo, the solids were collected, rinsed with water, and then rinsed with ethanol. Rrecrystallization was carried out from dimethyl formamide: 942 mg (78%) yield; mp 275°–276° C.; TLC (n-butanol/acetic acid/water [5:2:3]), $R_f$=0.47; IR (KBr pellet) 3361,1700, 1627, 1579, 1506, 1472, 1410, 1328, 1115, 1053 cm$^{-1}$; $^1$H NMR (dimethyl-$d_6$ sulfoxide) δ9.16 (2H, s, 2,5-acetamido NH), 7.80 (2H, brq, 3- and 6-carbamyl H), 3.96 (4H, s, methylenes), 3.65 and 3.37 (12H, 2 s, methoxys, no assignments made), 2.70 (6H, d, J=4.5 Hz, 3- and 6-carbamyl methyls); mass spectrum (EI mode) m/z 426 (P$^+$).

2,5-Bis(chloroacetamido)-3,6-bis(methylcarbamyl)-1,4-dimethoxybenzene (12): To 497 mg (1.40 mmol ) of 9.2HCl, dissolved in 15 mL of dry dimethyl formamide were added 510 µL (6.30 mmol) of pyridine and 250 µL (3.14 mmol) of chloroacetyl chloride. After stirring the reaction mixture at room temperature for 6 hours, the solids were filtered off, rinsed with water, and dried: 431 mg (71%) yield; mp 146°–148° C. and then 317°–319° C. after thermal cyclization; TLC (ethyl acetate/methanol [9:1]), $R_f$=0.24; IR (KBr pellet) 3269, 1669, 1644, 1567, 1526, 1472, 1409, 1328, 1057 cm$^{-1}$; $^1$H NMR (dimethyl-$d_6$ sulfoxide) δ9.72 (2H, s, 2- and 5-acetamido NH, 7.87 (2H, brs, 3- and 6-carbamyl Hs), 4.22 (4H, s, methylenes), 3.65 (6H, s methoxys), 2.70 (6H, d, J=4.6 Hz, 3- and 6-carbamyl methyls); mass spectrum (EI, solids probe), m/z 434 (P$^+$, $^{35}$Cl$^{35}$Cl), 436 (P$^+$, $^{37}$Cl $^{35}$Cl) 438 (P$^+$, $^{37}$Cl$^{37}$Cl).

2,5-Bis(bromoacetamido)-3,6-bis(methylcarbamyl)-1,4-dimethoxybenzene (13): To a solution of 503 mg (1.42 mmol) of 9 .2HCl in 15 mL of dry dimethyl formamide were added sequentially, 533 µL (6.59 mmol) of pyridine and 282 µL (3.42 mmol) of bromoacetyl chloride. After allowing the mixture to stir at room temperature for 6 hours, the precipitated product was filtered off and rinsed with water and then rinsed with ethanol: 393 mg (53%) yield; mp 308°–310° C.; TLC (n-butanol/acetic acid/water [5:2:3]), $R_f$=0.58; IR (KBr pellet) 3380, 3278, 1681, 1638, 1551, 1472, 1411, 1325, 1238, 1047 cm$^{-1}$; $^1$H NMR (dimethyl-$d_6$ sulfoxide) δ9.72 (2H, s, 2- and 5-acetamido N(H), 7.87 (2H, brs, 3- and 6-carbamyl proton), 4.22 (4H, s, methylenes), 3.65 (6H, s, methoxys), 2.70 (6H, d, J=4.6 Hz, 3- and 6-carbamyl methyl); mass spectrum (EI mode) m/z 522, 524 and 526 (P$^+$ for the $^{79}$Br, $^{79}$Br; $^{79}$Br, $^{81}$Br; $^{81}$Br, $^{81}$Br combinations, respectively, at an intensity ratio of 1:2:1).

2,7-Bis (phenoxymethyl)-5,10-dimethoxyprimido[4,5-g]quinazoline-4,9(3H,8H)-dione (14): To a solution consisting of 40 mL of acetic acid and 4 mL of concentrated sulfuric acid, was added 394 mg (0.753 mmol) of 10. The resulting mixture was refluxed for 4 hours. After allowing the mixture to cool to room temperature, the greyish colored precipitate was collected, washed with acetic acid, and then washed with water to afford pure 14 as a yellow solid: 260 mg (71%) yield; dec pt 290° C.; TLC (ethyl acetate/methanol [9:1]), $R_f$=0.56; IR (KBr pellet) 2967, 1687, 1630, 1599, 1497, 1463, 1427, 1239, 1206, 1066 cm$^{-1}$; $^1$H NMR (dimethyl-$d_6$ sulfoxide) δ7.32 (4H, t, J=7.4 Hz, aromatic, no assignments made), 7.08 ( 4H, d, J=7.8 Hz, aromatic, no assignments made), 6.98 ( 4H, t, J=7.4 Hz, aromatic, no assignments made), 5.02 ( 4H, s, methylenes), 3.81 (6H, s, methoxys); mass spectrum (EI mode), m/z 486 (P$^+$). Anal. Calcd for $C_{26}H_{22}N_4O_6$: C, 64.19; H, 4.56; N, 11.52. Found: C, 64.09; H, 4.52; N, 11.31.

2,7-Bis (methoxymethyl)-5,10-dimethoxy-3,8 dimethylpyrimido[4,5-g]quinazoline-4,9(3H,8H)-dione (15): To 100 mL acetic acid and 4 mL concentrated sulfuric acid, was added 1.80 g (4.22 mmol) of 11 and the mixture was heated at 100° C. for 5 hours. After evaporating the solvents down to ca 5 mL, the oily residue was poured over 100 mL of ice water, neutralized with sodium carbonate, and the resulting solution extracted with 3×100 mL portions of chloroform. The combined extracts were evaporated to a small volume, placed on a silica column, and purified by flash chromatography employing ethyl acetate as the eluant. The product fraction was collected and evaporated to dryness. Recrystallization was carried out by redissolving the product in a minimum amount of chloroform followed by addition of hexane: 1.10 g (67%) yield; mp 223°–224° C.; TLC (ethyl acetate/methanol [9:1], $R_f$=0.22; IR (KBr pellet) 1688, 1614, 1474, 1428, 1375, 1342, 1269, 1097, 1036, 797 cm$^{-1}$; $^1$H NMR (dimethyl-$d_6$ sulfoxide) δ4.58 (4H, s, methylenes), 3.93, 3.62 and 3.42 (18H, 3×s, N- and O-methyls, no assignments made); mass spectrum (EI mode) m/z 390 (P$^+$). Anal. Calcd for $C_{18}H_{22}N_4O_6$· 0.3$H_2O$: C, 54.75; H, 5.74; N, 14.19. Found: C, 54.39; H, 5.63; N, 14.25.

2,7-Bis(chloromethyl)-5,10-dimethoxy-3,8-dimethylpyrimido [4,5-g]quinazoline-4,9(3H,8H)-dione (16): To a solution consisting of 15 mL of acetic acid and 0.5 mL of sulfuric acid, was added 333 mg (0.766 mmol) of 12. The resulting mixture was heated at 110° C. for 5.5 hours. After cooling the reaction mixture to room temperature, the solution was poured over ca 50 mL of water and then buffered to pH 6 with sodium acetate. The resulting yellow precipitate was filtered, washed with water, and then dried. The dried solid was recrystallized from ethanol: 219 mg (72%) yield; mp 273°–274° C.; TLC (ethyl acetate/methanol [9:1]), $R_f$=0.34; IR (KBr) 1677, 1607, 1434, 1347, 1324, 1269, 1071, 1032, 795, 690 cm$^{-1}$; $^1$H NMR (dimethyl-d$_6$ sulfoxide) δ4.92 (4H, s, methylenes), 3.95 (6H, s, methoxys), 3.59 (6H, s, 3- and 8- methyls); mass spectrum (EI), m/z 398 (P$^+$, $^{35}$Cl$^{35}$Cl), 400 (P$^+$, $^{37}$Cl$^{35}$Cl), 402 (P$^{30}$, $^{37}$Cl$^{37}$Cl). Anal. Calcd for C$_{16}$H$_{16}$Cl$_2$N$_4$O$_4$: C, 48.14; H, 4.04; N, 14.03. Found: C, 48.40; H, 4.03; N, 14.14.

2,7-Bis (bromomethyl)-5,10-dimethoxy-3,8-dimethylpyrimido[4,5-g]quinazoline-4,9(3H,8H)-dione (17). To a solution consisting of 15 mL of acetic acid and 0.5 mL of sulfuric acid, was added 243 mg (0.463 mmol) of 13. The resulting mixture was heated at 100° C. for 9.5 hours. After allowing the solution to cool to room temperature, the solvents were removed in vacuo to near dryness. The residue was triturated with water and the resulting solids filtered off. A second crop of solids was obtained by buffering the filtrate with sodium acetate to pH 6. The solids were combined, rinsed with water, and dried to afford the yellow-colored product 156 mg (69%) yield; mp 263° . 264° C.; TLC (ethyl acetate/methanol [9:1]), $R_f$=0.3; IR (KBr pellet) 1680, 1606, 1466, 1434, 1347, 1324, 1270, 1072, 1032, 690 cm$^{-1}$, $^1$H NMR (dimethyl-d$_6$ sulfoxide) δ4.92 (4H, s, methylenes), 3.95 (6H, s, methoxys), 3.59 (6H, s, 3-and 8-methyls); mass spectrum (EI mode) m/z 486, 488 and 490 (P$^+$ for the $^{79}$Br, $^{79}$Br; $^{79}$Br, $^{81}$Br; $^{81}$Br, $^{81}$Br combinations, respectively, at an intensity ratio of 1:2:1.

2,7-Bis(bromomethyl)-5,10-dihydroxypyrimido[4,5-g] quinazoline-4,9(3H,8H)-dione (18): To a solution of 217 mg (0.447 mmol) of 14 in 50 mL of dry benzene, was added 3.2 mL (3.20 mmol) of 1 M BBr$_3$ in methylene chloride. The resulting mixture was refluxed for 5 hours. Additional BBr$_3$ (1.3 mL, 1.3 mmol) was then added to the reaction mixture, and the mixture was refluxed for an additional 5 hours. After cooling the reaction mixture to room temperature, methanol was added to destroy the excess BBr$_3$, and the solvents were removed in vacuo. The yellowish-red solid residue was redissolved in 5 mL methanol and 75 mL of water added to the solution resulting in precipitation of a greenish-yellow solid. Filtration, and washing the solids with water, and then washing with diethyl ether gave pure 18: 137 mg (71%) yield; dec pt >285° C.; TLC (n-butanol/acetic acid/water [5:2:3]), $R_f$=0.42; IR (KBr pellet) 3328, 3024, 1649, 1669, 1419, 1271, 1245, 1225, 1038, 800 cm$^{-1}$; $^1$H NMR (dimethyl-d$_6$ sulfoxide) δ4.45 (4H, s, methylenes); mass spectrum, (EI solids probe), m/z 430, 432, and 434 (P$^+$ for the $^{79}$Br, $^{79}$Br; $^{79}$Br, $^{81}$Br; $^{81}$Br, $^{81}$Br combinations, respectively, at an intensity ratio of 1:2:1). Anal. Calcd for C$_{12}$H$_8$Br$_2$N$_4$O$_4$·0.5H2O: C, 32.68; H, 2.05; N, 12.70. Found: C, 32.84; H, 1.89; N, 12.10.

2,7-Bis(bromomethyl)pyrimido[4,5-g]quinazoline-4,5,9,10(3H,8H)-tetrone (19): To 105 mg (0.244 mmol) of 18 suspended in 15 mL of dry methanol, was added 61 mg (0.268 mmol) of dichlorodicyanobenzoquinone (DDQ) and the reaction left to stir at room temperature for 1 hour. The solids were filtered off, washed with methanol, and dried to afford pure 19: 95 mg (91%) yield; dec pt 274°–275° C.; TLC (n-butanol/acetic acid/water [5:2:3]), $R_f$=0.46; IR (KBr pellet) 3062, 3040, 2990, 2933, 1713, 1645, 1576, 1547, 1480, 1142 cm$^{-1}$; $^1$H NMR (dimethyl-d$_6$ sulfoxide) δ4.45 (4H, s, methylenes); mass spectrum (EI, solids probe), m/z 428, 430, and 432 (P$^+$ for the $^{79}$Br, $^{79}$Br; $^{79}$Br, $^{81}$Br, $^{81}$Br, $^{81}$Br combinations, respectively, in an intensity ratio of 1:2:1). Anal. Calcd for C$_{12}$H$_6$Br$_2$N$_4$O$_4$; C, 33.52; H, 1.41; N, 13.03. Found: C, 33.89; H, 1.31; N, 12.50.

2,7-Bis(hydroxymethyl)-5,10-dihydroxy-3,8-dimethylpyrimido[4,5-g]quinazoline-4,9(3H,8H)-dione (20): To 172 mg 10.441 mmol) of 15, suspended in 50 mL of dry benzene, was added an excess of 99% BBr, (up to 10 fold excess). The resulting mixture was refluxed for 7 hours. After cooling the reaction mixture to room temperature, methanol was added to quench the reaction. The solvent was evaporated off in vacuo and the product purified by rinsing successively with water and methanol and then dried: 106.5 mg (72%) yield; dec pt >245° C. IR (KBr pellet) 3384, 1645, 1618, 1443, 1430, 1379, 1325, 1209, 1079, 965, 793 cm$^{-1}$; $^1$H NMR (dimethyl-d$_6$ sulfoxide) 11.86 (2H, s, 5- and 10-hydroxyls), 4.62 (4H, s, methylenes), 3.61 (6H, s, 3- and 8- methyls); mass spectrum (EI model m/z 334 (P$^+$).

2,7-Bis(chloromethyl)-5,10-dihydroxy-3,8-dimethylpyrimido[4,5-g]quinazoline-4,9(3H,8H)-dione (21): To a solution of 105 mg (0.313 mmol) of 20 in 10 mL of dry dimethyl formamide, were added 66 mg (1.56 mmol) of LiCl and 191 mg (1.56 mmol) of dimethylaminopyrldine. To this mixture was added 120 μL (1.56 mmol ) of methanesulfonyl chloride and the resulting solution gently heated with a heat gun until it became homogenous. After stirring this mixture at room temperature for 6 h, it was combined with 100 mL of water and the resulting mixture allowed to stir for an additional 2 hours. The resulting yellow precipitate was filtered, rinsed with water, and dried: 99 mg (85%) yield; mp >275° C. dec; IR (KBr pellet) 3036, 1645, 1603, 1421, 1372, 1343, 1270, 1240, 1015, 794 cm$^{-1}$; $^1$H NMR (dimethyl-d$_6$ sulfoxide) δ11.84 (2H, s, 5- and 10-hydroxyl) 4.95 (4H, s, methylenes), 3.65 (6H, s, 3- and 8- methyls); mass spectrum (EI, solids probe), m/z 370 (P$^+$, $^{35}$Cl$^{35}$Cl), 372 (P$^+$, $^{37}$Cl$^{35}$Cl), 374 (P$^+$, $^{37}$Cl$^{37}$Cl). Anal. Calcd for C$_{14}$H$_{12}$Cl$_2$N$_4$O$_4$: C, 45.30, H, 3.26; N, 15.09. Found: C, 45.76; H, 3.47; N, 13.99.

2,7-Bis(chloromethyl)-3,8-dimethylpyrimido[4,5-g] quinazoline-4,5,9,10(3H8H)-tetrone (22): To 32 mg (0.088 mmol) of 21, suspended in 3 mL of 75% aqueous acetonitrile, was added 96 mg (0.175 mmol) of ceric ammonium nitrate (CAN). The starting material immediately went into solution, and after ca 5 minutes of reaction time, formation of a precipitate was observed. After stirring for an additional 15 minutes, 3 mL of water was added to the reaction mixture and the resulting solution extracted several times with chloroform. The extracts were dried (Na$_2$SO$_4$) and then evaporated to a small volume. Addition of hexane resulted in crystallization of pure product: 16 mg (49%) yield; dec pt >275° C.; TLC (n-butanol/acetic acid/water [5:2:3]), $R_f$=0.5; IR (KBr pellet) 3440, 1711, 1659, 1569, 1525, 1441, 1386, 1373, 1067, 978 cm$^{-1}$; $^1$H NMR (dimethyl-d$_6$ sulfoxide) δ4.97 (4H, s, methylenes), 3.61 (6H, s, 3- and 8-methyls); mass spectrum (EI, solids probe), m/z 370 (P$^+$+2, $^{35}$Cl$^{35}$Cl), 372 (P$^{30}$+2, $^{35}$Cl), 374 (P$^+$+2, $^{37}$Cl$^{37}$Cl$^{\pm}$Cl). Anal. Calcd for C$_{14}$H$_{10}$Cl$_2$N$_4$O$_4$: C, 45.55; H, 2.73; N, 15.18. Found: C, 45.30; H, 2.92; N, 14.27. The nitrogen percentage obtained experimentally deviates widely from the theoretical values. The $^1$H NMR and mass spectra indicate that the material is pure and that the assigned structure correct, however.

2-Acetamido-3,6-dicarbamyl-1,4-dimethoxybenzene (23) was prepared by the two-step process described below:

A mixture consisting of 1.74 g (6.47 mmol) of 3, 200 mg of 5% Pd on carbon, and 200 mL of methanol were shaken under 50 psi of $H_2$ for 3 hours. The crystallized product was separated from the catalyst by adding 200 mL of acetic acid, heating the mixture, and filtering through CELITE. The solvents were evaporated in vacuo to afford a yellow oily residue, which upon addition of ethanol and sonication afforded the amine as a crude tan colored solid, 1.25 g (81%) yield. For further purification, the solid was dissolved in hot dimethyl formamide and decolorized with activated charcoal. The solution was then filtered through CELITE and the solvent evaporated off to give an oily residue. Addition of ethanol and then sonication resulted in crystallization of the pure amine as white flakes: mp 272°–273° C.; TLC (chloroform/methanol[9:1]), $R_f$=0.31; IR (KBr pellet) 3427, 3394, 3182, 1639, 1589, 1465, 1453, 1418, 1399, 1140 $cm^{-1}$; $^1$H NMR (dimethyl-$d_6$, sulfoxide) $\delta$7.65, 7.56 and 7.48 (4H, 3 brs, 3- and 6-carbamyls, no assignments made), 6.39 (1H, s, 4-H), 6.27 (2H, brs, amino), 3.78 and 3.64 (6H, 2 s, 3- and 6-methoxys, no assignments made); mass spectrum (EI mode), m/z 239 ($P^+$). Anal. Calcd for $C_{10}H_{13}N_3O_4$: C, 50.21; H, 5.48; N, 17.56. Found: C, 49.95; H, 5.44; N, 17.21.

To a solution consisting of 20 mL acetic anhydride and 10 mL of acetic acid, was added 225 mg (0.939 mmol) of the product obtained above. The mixture was heated at 40° C. for 4.5 hours. After adding methanol to quench the reaction, the solvents were evaporated in vacuo, and the residue was dissolved in hot dimethyl formamide and then treated with activated charcoal. Filtration through CELITE, evaporation of the solvent in vacuo, followed by addition of ethanol, and then sonication afforded the desired product as a white solid: 206 mg (78%) yield; mp 257°–258° C.; TLC (n-butanol-acetic acid-water[5:2:3]), $R_f$=0.52; IR (KBr pellet) 3172, 3167, 1697, 1658, 1517, 1456, 1411, 1383, 1253, 1112 $cm^{-1}$; $^1$H NMR (dimethyl-$d_6$sulfoxide) $\delta$9.38 (1H, brs, acetamido NH), 7.72, 7.64 and 7.43 (4H, 3 brs, 3- and 6- carbamyls, no assignments made) 7.24 (1H, s, aromatic), 3.78 and 3.66 (6H, 2 s, 1- and 4-methoxys, no assignments made), 1.97 (3H, brs, acetamido methyl); mass spectrum (EI mode), m/z 281 ($P^+$).

7-Methoxycarbonyl-5,8-dimethoxy-2-methylquinazolin-4(3H)-one (24) was prepared by the following two-step procedure:

A mixture consisting of 50 mL of ethanol, 30 mL of 10% aqueous sodium hydroxide, and 523 mg (1.86 mmol) of 23 was refluxed for 24 hours. The solvent was evaporated off and the resulting residue was redissolved in a minimum amount of water. To remove the salts by anion exchange chromatography (BIO-RAD, AG1-X4, 200–400 mesh), the aqueous solution obtained above was made basic and placed on the column. After washing the column with water, the product was eluted off with dilute aqueous hydrochloric acid. The eluant was evaporated to dryness in vacuo and the solid residue was dissolved in hot ethanol. Addition of ethyl acetate afforded the ring closed product as the carboxylic acid: 383 mg (78%) yield; TLC (isopropanol-water-ammonia[7:1:2], $R_f$=0.47; $^1$H NMR (dimethyl-$d_6$ sulfoxide) $\delta$7.08 (1H, s, 6-H), 3.87 (6H, s, methoxys) 2.42 (3H, s, 2-methyl); mass spectrum (EI mode), m/z 264 ($P^+$).

The carboxylic acid, 383 mg (1.45 mmol), 50 mL of methanol and 2 mL of concentrated sulfuric acid were combined and refluxed for 10 hours. The reaction mixture was evaporated in vacuo to an oil, which was poured over 50 mL of ice water. The solution was neutralized with sodium carbonate, and was then extracted with 3×75 mL portions of chloroform. The organic extracts were dried ($Na_2SO_4$) and were evaporated to a small volume. Addition of hexane afforded 24 as white flakes: 277 mg (69%) yield; mp 205°–207° C.; TLC (isoproponol-water-ammonia[7:1:2]), $R_f$=0.61; IR (KBr pellet) 1711, 1682, 1634, 1465, 1436, 1352, 1291, 1263, 1236, 1109 $cm^{-1}$; $^1$H NMR (dimethyl-$d_6$ sulfoxide) $\delta$6.99 (1H, s, 6-H), 3.89 and 3.83 (9H, 2 s, methoxys, no assignments made), 2.33 (3H, H, s, 2-methyl); mass spectrum (EI mode), m/z 278 ($P^+$). Anal. Calcd for $C_{13}H_{14}N_2O_5 \cdot 0.2 H_2O$: C, 55.40; H, 5.15; N; 9.94. Found: C, 55.54; H, 4.86; N, 10.05.

7-Methoxycarbonyl-5,8-dimethoxy-2-methyl-6-nitroquinazolin-4(3H)-one (25): To 703 mg (2.53 mmol) of 24, suspended in 25 mL of dry acetonitrile chilled to 10° C., was added 434 mg (2.78 mmol) of $NO_2BF_4$. After stirring the reaction mixture for 10 minutes at room temperature, the homogeneous solution was poured into 100 mL of ice water. The resulting yellow solid was filtered, washed with water, and dried to afford pure product: 621 mg (76%) yield; mp 246°–247° C.; TLC (ethyl acetate-ethanol[95:5]), $R_f$=0.35; IR (KBr pellet) 2957, 1745, 1679, 1621, 1537, 1443, 1350, 1291, 1239 $cm^{-1}$; $^1$H NMR (dimethyl-$d_6$ sulfoxide) $\delta$3.99, 3.91 and 3.87 (9H, 3 s, methoxys, no assignments made), 2.42 (3H, s, 2-methyl); mass spectrum (EI mode), m/z 323 ($P^+$). Anal. Calcd for $C_{13}H_{13}N_3O_7$: C, 48.30; H, 4.05; N; 13.00. Found: C, 48.32; H, 3.94; N, 12.82.

6-(Phenoxyacetamido)-7-methoxycarbonyl-5,8-dimethoxy-2-methylquinazolin-4(3H)-one (26) was prepared by the two-step procedure described below:

A mixture consisting of 581 mg (1.80 mmol) of 25, 50 mg 5% Pd/C, and 100 mL of methanol was shaken under 50 psi of $H_2$ for 4 hours. The solution was filtered through CELITE and the solvents were evaporated off to afford the crude 6-amino derivative as an amber-colored solid residue. The residue was recrystallized by dissolution in the minimum amount of hot ethanol followed by addition of hexane: Yield 483 mg (92%); mp 209°–210° C.; TLC (ethyl acetate-ethanol[95:5]), $R_f$=0.25; IR (KBr pellet) 2944, 1716, 1670, 1641, 1459, 1434, 1333, 1308, 1231 1046 $cm^{-1}$; $^1$H NMR (dimethyl-$d_6$ sulfoxide) $\delta$5.25 (2H, s, 6-amino), 3.88, 3.87 and 3.70 (9H, 3 s, methoxys, no assignments made), 2.26 (3H, s, 2-methyl); mass spectrum (EI mode), m/z 293 ($P^+$). Anal. Calcd for $C_{13}H_{15}N_3O_5 \cdot 0.1 H_2O$: C, 52.92; H, 5.19; N; 14.24. Found: C, 52.73; H, 4.93; N, 14.01.

To 185 mg (0.630 mmol) of the amine obtained above, suspended in 20 mL of dry benzene, were added 100 µL (0.725 mmol) of phenoxyacetyl chloride and 60 µL (0.742 mmol) of pyridine. The resulting mixture was stirred at room temperature for 3.5 hours. Evaporation of the solvents in vacuo to a solid residue, followed by addition of ca 5 mL of aqueous ethanol and sonication, afforded 226 mg of crude product. The compound was then dissolved in chloroform and the solution decolorized with activated charcoal. After removing the charcoal, the solvent was reduced to a small volume and the product crystallized by addition of hexane: 216 mg (80%) yield; mp 225°–225° C.; TLC (ethyl acetate-methanol[91:]), $R_f$=0.32; IR (KBr pellet) 3389, 1726, 1627, 1629, 1514, 1497, 1456, 1239, 1226, 1062 $cm^{-1}$; $^1$H NMR (dimethyl-$d_6$ sulfoxide) $\delta$12.25 (1H, s, 3-NH), 9.73 (1H, s, acetamido-NH), 7.37–7.31 and 7.01–6.98 (5H, complex multiplets, aromatic), 4.69 (2H, s, methylene), 3.93, 3.74 and 3.67 (9H, 3 s, methoxys, no assignments made), 2.36 (3H, s, 2-methyl); mass spectrum (EI mode), m/z 427 ($P^+$). Anal. Calcd for $C_{21}H_{21}N_3O_7$: C, 59.01; H, 4.95; N, 9.83. Found: C, 59.04; H, 4.84; N, 9.67.

2-(Phenoxyacetamido)-5,10-dimethoxy-7-methylpyrimido[4,5-g]quinazoline-4,9(3H,8H)-dione (27): A mixture of 309 mg (0.723 mmol) of 26, 3.5 mg (0.072 mmol) of sodium cyanide, and 50 mL of saturated methanolic ammonia was heated in a steel bomb at 80° C. for 24 hours. The solvent was then evaporated in vacuo and the residue was dissolved in a small volume of water. The product crystallized from solution upon adjusting the pH to 6 with concentrated hydrochloric acid. The yellow product was recrystallized from aqueous dimethyl formamide: 177 mg (62%) yield; dec'pt 312°–314° C.; TLC ([5:2:3]), $R_f$=0.6; IR (KBr pellet) 2971, 2933, 2874, 1687, 1627, 1600, 1498, 1279, 1211, 1072 cm$^{-1}$; $^1$H NMR (dimethyl-$d_6$ sulfoxide) δ7.32 (2H, t, J=7.6 Hz, aromatic, no assignments made) 7.09 (2H, d, J=8.8 Hz, aromatic, no assignments made), 6.98 (1H, t, J=7.1 Hz, aromatic, no assignments made), 5.01 (2H, s, methylene), 3.88 and 3.81 (6H, 2 s, 5- and 10-methoxys, no assignments made), 2.35 (3H, s, 7-methyl); mass spectrum (EI mode), m/z 394 (P$^+$). Anal. Calcd for $C_{20}H_{18}N_4O_5 \cdot 0.75 H_2O$: 58.89; H, 4.81; N, 13.73. Found: C, 58.64; H, 4.66; N, 13.67.

2-(Chloromethyl)-5,10-dihydroxy-7-methylpryimido[4,5-g]quinazoline-4,9(3H,8H)-dione (28) was prepared by the two-step synthesis described below.

To a suspension consisting of 191 mg (0.483 mmol) of 27 in 100 mL of dry benzene was added 3.8 mL (3.80 mmol) of 1M BBr$_3$. The resulting mixture was refluxed for 24 hours. After cooling the solution to room temperature, methanol was added to quench the reaction. The solvents were removed in vacuo and the precipitated residue was combined with ca 20 mL of water. The resulting solid (the bromomethyl derivative of 28) was filtered, rinsed with water, and then rinsed with diethyl ether: Yield 105.4 mg (62%); mp >250° C. dec; TLC (n-butanol-acetic acid-water [5:2:3]) $R_f$=0.17; IR (KBr) 3052, 3041, 3021, 1654, 1619, 1416, 1376, 1273, 1226, 1039 cm$^{-1}$; $^1$H NMR (dimethyl-$d_6$ sulfoxide) δ12.74 (2H, brs, 5- and 10-OH), 11.88 and 11.67 (2H, 2 brs, 3- and 8-NH, no assignments made), 4.44 (2H, s, methylene), 2.39 (3H, d, J=3.7 Hz, 7-methyl coupled to 8-NH); mass spectrum (EI mode), m/z 354 (P$^+$, $^{79}$Br), 356 (P$^+$, $^{81}$Br).

In 5 ml of dry dimethyl formamide, 103 mg (0.291 mmol) of the bromomethyl derivative and 123 mg (2.91 mmol) of lithium chloride were combined and the resulting mixture was stirred at room temperature for 2.5 hours. The solvent was evaporated in vacuo to an oily residue with minimal heating. The addition of ca 20 ml of water precipitated the product, which was filtered and then was washed with water: Yield 82 mg (91%); mp>290° C. dec; TLC (n-butanol—acetic acid—water[5:2:3]) $R_f$=0.25; IR (KBr) 3070, 3062, 1657, 1621, 1491, 1418, 1377, 1272, 1225, 1040 cm$^{-1}$; $^1$H NMR (dimethyl-$d_6$ sulfoxide) δ11.88 and 11.77 (2H, 2 brs, no assignments made), 4.57 (2H, s methylene), 2.39 (3H, s, 2-methyl); mass spectrum (EI mode, solids probe), m/z 274 (P$^+$-Cl).

1,4-Bis(methycarbamyl-2,5-dimethoxy-6-nitrobenzene (29): To 75 mL of a 10% methanolic methylamine solution was added 1.15 g (3.84 mmol) of 4. After stirring the reaction mixture at room temperature for 5 hours, the solvent was evaporated to dryness and the oily residue was dissolved in a minimum amount of hot ethanol. Addition of hexane to this solution afforded 29 as an orange-colored solid: 1.03 g (91%) yield; mp 233°–235° C.; TLC (chloroform-ethanol [95:5]), $R_f$=0.25; IR (KBr pellet) 3323, 1661, 1649, 1563, 1543, 1484, 1403, 1379, 1231, 1061 cm$^{-1}$; $^1$H NMR (dimethyl-$d_6$ sulfoxide) δ8.48 (2H, 2 overlapping quartets, 1- and 4-carbamyl protons), 7.38 (1H, s, 3-H aromatic), 3.86 and 3.74 (6H, 2 s, 2- and 5-methoxys, no assignments made), 2.80 and 2.70 (6H, 2 d, J=2.4 Hz, 1- and 4-carbamyl methyls, no assignments made); mass spectrum (EI mode), m/z 297 (P$^+$).

2-(Chloroacetamido)-1,4-bis(methylcarbamyl)-3,6-dimethoxybenzene (30) was prepared by the two-step procedure described below:

A mixture consisting of 1.04 g (3.49 mmol) of 29, 200 mg of 5% Pd/C, and 200 mL of methanol was shaken overnight under 50 psi of H$_2$. The spent Pd/C was removed by filtering the reaction mixture through a CELITE pad using methanol as the eluant. The filtrate was evaporated to an oily residue, which was dissolved in 20 mL of hot ethanol. Addition of hexane afforded a pinkish-colored solid, which was rinsed with cold water: 700 mg (75%) yield; TLC (chloroform methanol [9:1]), $R_f$=0.56; $^1$H NMR (dimethyl-$d_6$ sulfoxide) δ8.14 and 8.09 (2H, 2 broad quartet, J=2.7 Hz, 1- and 4-carbamyls protons), 6.33 (1H, s, 5-H aromatic), 5.93 (2H, d, J=2.8 Hz, 2-amino), 3.75 and 3.61 (6H, 2 s, 3- and 6-methoxys, no assignments made), 2.78 and 2.75 (6H, 2 d, J=2.3 Hz, 1- and 4-carbamyl-methyls, no assignments made); IR (KBr pellet) 3337, 3321, 1644, 1631, 1589, 1550, 1461, 1418, 1358, 1224 cm$^{-1}$; mass spectrum (EI mode), m/z 267 (P$^+$).

In 100 mL of dry dimethyl formamide, 3.0 g (11.2 mmol) of the product obtained above, 4.45 mL (55 mmol) dry pyridine, and 1.31 mL (17.0 mmol) of chloroacetyl chloride were combined and stirred at room temperature for 2 hours. The solvent was then evaporated in vacuo without heating to an oily residue, which was combined with ca 100 mL of water and sodium bicarbonate such that the pH ca 7. The solvent was then evaporated in vacuo to a dry residue, which was extracted several times with chloroform. The chloroform protions were combined, dried (Na$_2$SO$_4$), and evaporated to dryness to afford a tan-colored solid: 3.4 g (90%) of crude 30. For pure material, the following procedure was carried out: After dissolving 163 mg of compound 30 in the minimum amount of chloroform and allowing the solution to sit for 1 hour, the oily residue was filtered off and hexane was added until the solution became cloudy. After sitting for 24 hours, the white solids were filtered and dried to give 144 mg of 30: mp 228°–229° C.; TLC (ethyl acetate-methanol [9:1]), $R_f$=0.21; IR (KBr pellet) 3275, 1667, 1641, 1564, 1525, 1477, 1413, 1290, 1240, 1079 cm$^{-1}$; $^1$H NMR (dimethyl-$d_6$ sulfoxide) δ9.69 (1H, s, acetamido proton), 8.24 (1H, s, J=2.4 Hz, carbamyl methyl, no assignment made), 7.83 (1H, brq, J=2.4 Hz, carbamyl methyl, no assignment made), 7.19 (1H, s, 5-H aromatic) 4.20 12H, s, methylene), 3.77 and 3.63 (6H, 2 s, 3- and 6-methoxys, no assignments made), 2.80 and 2.67 (6H, 2 d, J=2.3 Hz, 1- and 4-carbamyl methyls, no assignments made); mass spectrum (EI mode), m/z 343 (P$^+$, $^{35}$Cl), 345 (P$^+$, $^{37}$Cl).

2-(Chloroacetamido)-1,4-bis(methylcarbamyl)-3,6-dimethoxy-5-nitrobenzene (31): To 50 mL of red fuming nitric acid, chilled to 0° C., was added 2.3 g (6.69 mmol) of 30. After stirring at 0° C. for 45 minutes, 100 mL of ice water was added and the mixture quickly extracted with ethyl acetate. The ethyl acetate extract was dried over Na$_2$SO$_4$, evaporated down to a small volume, and placed on a silica gel column. Gradient chromatography (ethyl acetate to 5% methanolic ethyl acetate) afforded the desired product as a pure white solid: 1.5 g (58%) yield; TLC (ethyl acetate-methanol [9:1]), $R_f$=0,40; mp 259°–260° C.; IR (KBr pellet) 3370, 1676, 1651, 1568, 1534, 1472, 1404, 1373, 1315, 1054 cm$^{-1}$; $^1$H NMR (dimethyl-$d_6$ sulfoxide) δ9.99 ($^1$H, s, acetamido proton), 8.64 and 8.28[2H, 2 s, J=2.3 Hz, 1- and 4-carbamyl protons, no assignments made), 4.25 (2H, s, methylene), 3.79 and 3.68 (6H, 2 s, 3- and 6-methoxys, no assignments made), 2.73 (6H, 2 overlapping d, J=4.4 Hz, 1- and 4-carbamyl methyls, no assignments made); mass spectrum (EI mode), m/z 388 ($P^+$), 390 ($P^+$, $^{37}Cl$).

2-(Chloroacetamido)-1,4-bis(methylcarbamyl)-5-amino-3,6-dimethoxybenzene (32): A mixture consisting of 930 mg (2.39 mmol) of 31, 100 mg 5% Pd/C, and 200 mL of methanol was shaken under 50 psi of H, for 2 hours. The spent Pd/C was removed by filtration through a CELITE pad using methanol as eluant. The solvent was evaporated off and the solid residue redissolved in chloroform. Flash chromatography using ethyl acetate as eluant gave the desired product as a white solid: 749 mg (87%) yield; mp 242°–244° C.; TLC lethyl acetate-methanol [9:1]), $R_f$=0.29; IR (KBr pellet) 3275, 1698, 1682, 1629, 1578, 1536, 1456, 1426, 1407, 1329 cm$^{-1}$; $^1$H NMR (dimethyl-d$_6$ sulfoxide) δ9.34 (1H, s, acetamido proton), 8.13 and 7.69 (2H, 2 s, J=2.3 Hz, 1- and 4-carbamyl protons, no assignments made), 5.64 (2H, s, 5-amino), 4.16 (2H, s, methylene), 3.63 and 3.57 (6H, 2 s, 3- and 6-methoxys, no assignments made), 2.77 and 2.69 (6H, 2 d, J=2.3 Hz 1- and 4-carbamyl methyls, no assignments made); mass spectrum (EI mode), m/z 358 ($P^+$, $^{35}Cl$), 360 ($P^+$, $^{37}Cl$).

2-(Chloromethyl)-5,10-dimethoxy-3,7,8-trimethylpyrimido[4,5-g]quinazoline-4,9(3H,8H)-dione (33 was synthesized by the following two-step procedure:

In 50 mL of dry dimethyl formamide were added 663 mg (1.85 mmol) of 32, 164 µL (2.03 mmol) of dry pyridine and 145 (2.03 mmol) of acetyl chloride. After stirring the mixture at room temperature for 0.5 hours, the solvent was removed in vacuo and the solid residue was dried for 1 hour: TLC (n-butanol—acetic acid—water[5:2:3]), $R_f$=0.5; $^1$H NMR (dimethyl-d$_6$ sulfoxide) δ 9.69 (1H, s, acetamido NH, no assignment made), 9.35 (1H, brs, acetamido NH, no assignment made), 7.82 and 7.72 (2H, 2 brs, carbamyl protons, no assignments made), 4.21 (2H, s, methylene), 3.65 and 3.64 (6H, 2 s, 5- and 10-methoxys, no assignments made), 2.70 (6H, d, J=3.9 Hz, carbamyl methyls), 1.98 (3H, brs, acetyl); mass spectrum (EI mode), m/z 400 ($P^+$, $^{35}Cl$), 402 ($P^+$, $^{37}Cl$).

To the dried residue obtained above were added 50 mL of acetic acid and 3 mL of concentrated sulfuric acid. The resulting solution was heated at 100° C. for 4 hours. The solution was then evaporated/a vacuo to an oily residue, to which was added 50 mL of water. After neutralizing the solution to ca pH 7 with sodium bicarbonate, the solution was extracted several times with ethyl acetate (until extracts contained no product). The ethyl acetate extracts were dried over Na$_2$SO$_4$ and evaporated to residue. Flash chromatography of the residue on silica gel using ethyl acetate as eluant afforded pure product. Recrystallization was carried out from ethanol: overall yield 365 mg (54%); mp 214°–216° C.; TLC (ethyl acetate-methanol [8:2]), $R_f$=0.40; IR (KBr) 1687, 1678, 1605, 1466, 1422, 1334, 1322, 1261, 1067, 1030 cm$^{-1}$; $^1$H NMR (dimethyl-di sulfoxide) δ4.90 (2H, s, methylene), 3.93 and 3.92 (6H, 2 s, 5- and 10-methoxys, no assignments made), 3.58 and 3.50 (6H, 2 s, N(3- and 8-) methyls, no assignments made), 2.60 (3H, s, 7-methyl); mass spectrum (EI mode), m/z 364 ($P^+$, $^{35}Cl$), 366 ($P^+$, $^{37}Cl$). Anal. Calcd for C$_{16}$H$_{17}$ClN$_4$O$_4$: C, 52.68; H, 4.69; N, 15.35. Found: C, 52.49; H, 4.59; N, 15.64.

2-(Chloromethyl)-3,7,8-trtmethylpyrimido[4,5-g] quinazoline-4,5,9,10 (3H,8H)-tetrone (34): To 144 mg (0.395 mmol) of 33, dissolved in 50 mL of acetonitrile, was added 650 mg (1.19 mmol) of ceric ammonium nitrate in 15 mL of water. After stirring at room temperature for 2 hours, the solvents were evaporated in vacuo and the residue was combined with ca 20 mL of water. The aqueous solution was extracted with chloroform until product was no longer observed in the extracts. Pure product was obtained by drying (Na$_2$SO$_4$) and evaporating off the chloroform, and then prompting crystallization by addition of ethanol to the residue: 365 mg (54%) yield; mp>360° C. dec; TLC (n-butanol—acetic acid—water [5:2:3]), $R_f$=0.34; IR (KBr) 1710, 1656, 1563, 1522, 1431, 1385, 1362, 1306, 1068, 976 cm$^{-1}$; $^1$H NMR (dimethyl-d$_6$ sulfoxide) δ4.97 (2H, s, methylene), 3.60 (3H, s, 3-methyl), 3.53 (3H, s, 8-methyl), 2.68 (3H, s, 7-methyl)l mass spectrum (EI mode, solids probe), m/z 336 ($P^+$+2, $^{35}Cl$), 338 ($P^+$+2, $^{37}Cl$). Anal. Calcd. for C$_{14}$H$_{11}$ClN$_4$O$_4$: C, 50.23; H, 3.31; N, 16.74. Found: C, 50.02; H, 3.20; N, 16.67.

2-(Chloromethyl)-5,10-dihydroxy-3,7,8-trimethylpyrimido[4,5-g]quinazoline-4,9(3H,8H)-dione (35): To a solution consisting of 12.5 mg (0.037 mmol) of 34 in 20 ml chloroform was added 20 ml of aqueous sodium dithionite. The resulting mixture was shaken 3 times in a separatory funnel. The chloroform layer was removed, washed with water and then dried over Na$_2$SO$_4$. The extract was evaporated in vacuo to ca 2 ml, which upon addition of hexane afforded the desired product as a bright-yellow solid: Yield 9.6 mp (77%); mg>265° C. dec: TLC (n-butanol—acetic acid—water [51213]), $R_f$=0.22; IR (KBr) 1642, 1601, 1454, 1423, 1385, 1373, 1336, 1235, 1010, 796 cm$^{-1}$; $^1$H NMR (dimethyl-d$_6$ sulfoxide) δ12.00 and 11.73 (2H, 2 s, 5- and 10-hydroxy, no assignments made), 4.93 (2H, s, methylene), 3.64 and 3.55 (6H, 2 s, 3- and 8-methyls, no assignments made), 2.61 (3H, s, 7-methyl); mass spectrum (EI modes, solids probe), m/z 336 ($P^+$, $^{35}Cl$), 338 {$P^+$, $^{37}Cl$).

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A pyrimido[4,5-g]quinazoline dione derivative having the structural formula:

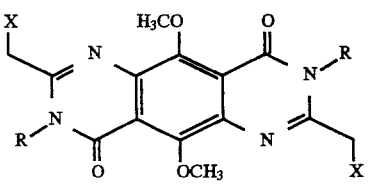

wherein:

R is H or CH$_3$; and

X is Cl or Br.

2. A derivative according to claim 1 in which R is hydrogen.

3. A pyrimido[4,5-g]quinazoline dione derivative having the structural formula:

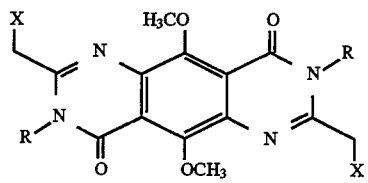

wherein

R is CH₃ and X is Cl or Br.

4. A derivative according to claim 1 in which X is chloro.
5. A derivative according to claim 1 in which X is bromo.
6. A derivative according to claim 2 in which X is chloro.
7. A derivative according to claim 2 in which X is bromo.
8. A derivative according to claim 3 in which X is chloro.
9. A derivative according to claim 3 in which X is bromo.
10. A pyrimido[4,5-g]quinazoline dione derivative having the structural formula:

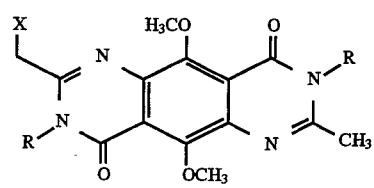

wherein:

R is H or CH₃; and

X is Cl or Br.

11. A derivative according to claim 10 in which R is CH₃ and X is Cl.

* * * * *